United States Patent
Prakash

(10) Patent No.: US 12,303,512 B2
(45) Date of Patent: May 20, 2025

(54) THERAPEUTICALLY ACTIVE COMPOUNDS AND THEIR METHODS OF USE

(71) Applicant: Servier Pharmaceuticals LLC, Boston, MA (US)

(72) Inventor: Chandra Agarwal Prakash, North Andover, MA (US)

(73) Assignee: Servier Pharmaceuticals LLC, Boston, MA (US)

(*) Notice: Subject to any disclaimer, the term of this patent is extended or adjusted under 35 U.S.C. 154(b) by 0 days.

(21) Appl. No.: 18/479,185

(22) Filed: Oct. 2, 2023

(65) Prior Publication Data

US 2024/0041892 A1    Feb. 8, 2024

Related U.S. Application Data

(62) Division of application No. 17/668,649, filed on Feb. 10, 2022, now Pat. No. 11,865,079.

(60) Provisional application No. 63/217,843, filed on Jul. 2, 2021, provisional application No. 63/149,075, filed on Feb. 12, 2021.

(51) Int. Cl.
| | | |
|---|---|---|
| A61K 31/53 | (2006.01) |
| A61K 9/00 | (2006.01) |
| A61K 45/06 | (2006.01) |
| C07D 401/04 | (2006.01) |
| C07D 401/14 | (2006.01) |

(52) U.S. Cl.
CPC ............ *A61K 31/53* (2013.01); *A61K 9/0019* (2013.01); *A61K 9/0053* (2013.01); *A61K 45/06* (2013.01); *C07D 401/04* (2013.01); *C07D 401/14* (2013.01)

(58) Field of Classification Search
None
See application file for complete search history.

(56) References Cited

U.S. PATENT DOCUMENTS

| | | |
|---|---|---|
| 2013/0190287 A1 | 7/2013 | Cianchetta et al. |
| 2017/0298045 A1 | 10/2017 | Cianchetta et al. |
| 2019/0161473 A1 | 5/2019 | Wang et al. |

FOREIGN PATENT DOCUMENTS

WO    2015003640 A1    1/2015

OTHER PUBLICATIONS

Konteantis et al. "Vorasidenib (AG-881): A First-in-Class, Brain-Penetrant Dual Inhibitor of Mutant IDH1 and 2 for Treatment of Glioma" ACS Med. Chem Lett. 2020, 11, 101-107 (Year: 2020).*
International Search Report and Written Opinion for International Application No. PCT/US2022/015994 dated May 3, 2022.

* cited by examiner

*Primary Examiner* — Adam C Milligan
*Assistant Examiner* — Jed A Kucharczk
(74) *Attorney, Agent, or Firm* — GOODWIN PROCTER LLP

(57) ABSTRACT

Provided are compounds useful for treating cancer and methods of treating cancer comprising administering to a subject in need thereof a purified compound described herein.

21 Claims, 1 Drawing Sheet

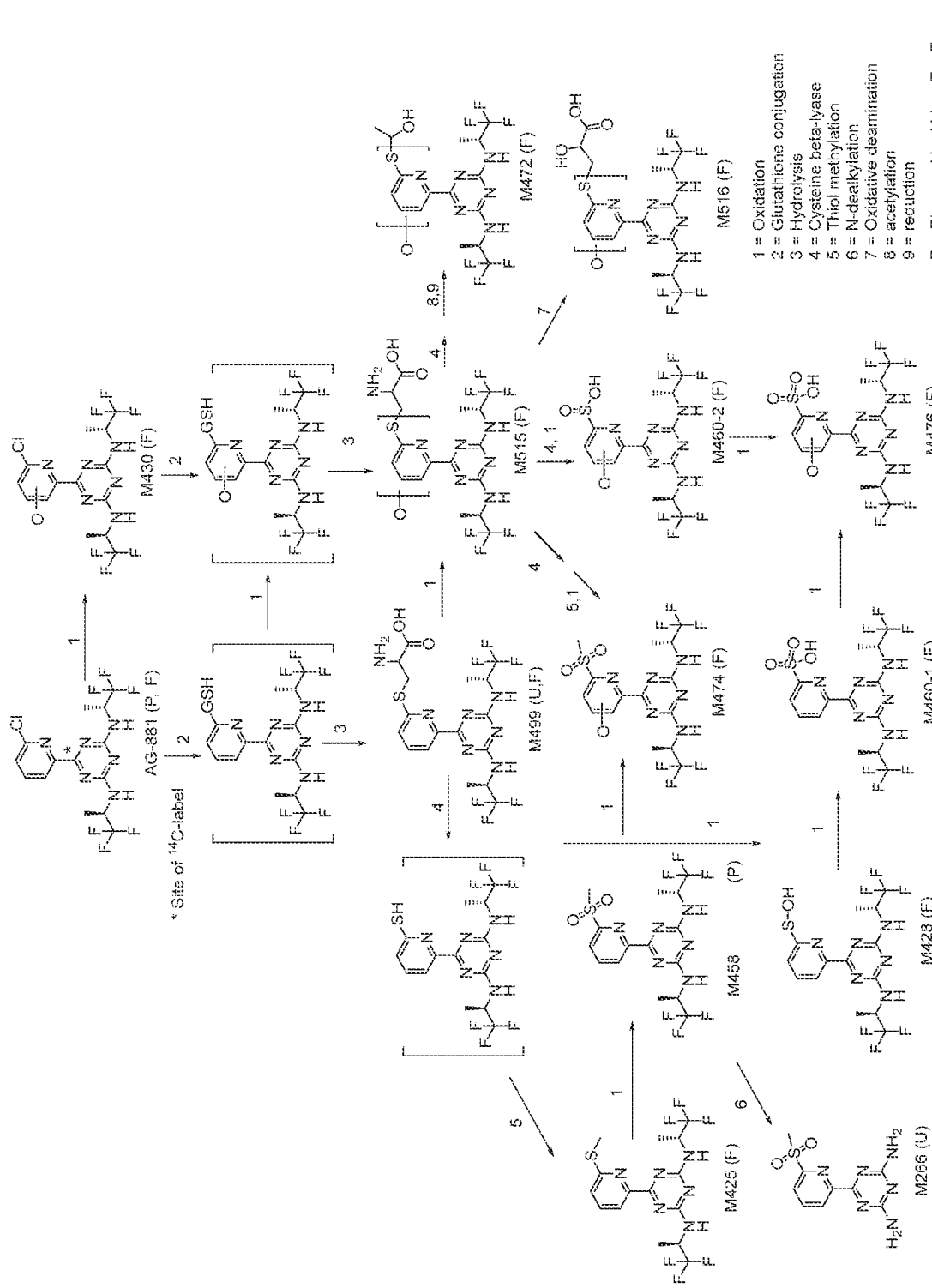

THERAPEUTICALLY ACTIVE COMPOUNDS AND THEIR METHODS OF USE

CLAIM OF PRIORITY

This application is a divisional of U.S. application Ser. No. 17/668,649, filed Feb. 10, 2022, which claims priority from U.S. provisional patent application No. 63/149,075 filed Feb. 12, 2021 and U.S. provisional patent application No. 63/217,843 filed Jul. 2, 2021, which is incorporated herein by reference in its entirety.

BACKGROUND OF THE INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December-2008) to UniProtKB; Kullmann et al., Submitted (June-1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate thereby reducing NAD (NADP$^+$) to NADH (NADPH), e.g., in the forward reaction:

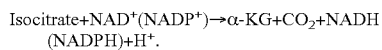

It has been discovered that mutations of IDH1 present in certain cancer cells result in a new ability of the enzyme to catalyze the NADPH-dependent reduction of α-ketoglutarate to R(−)-2-hydroxyglutarate (2HG). The production of R(−)-2-hydroxyglutarate (2HG) is believed to contribute to the formation and progression of cancer (Dang, L et al., Nature 2009, 462:739-44).

IDH2 (isocitrate dehydrogenase 2 (NADP$^+$), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing NAD (NADP$^+$) to NADH (NADPH), e.g., in the forward reaction:

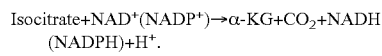

It has been discovered that mutations of IDH2 present in certain cancer cells result in a new ability of the enzyme to catalyze the NADPH-dependent reduction of α-ketoglutarate to R(−)-2-hydroxyglutarate (2HG). R(−)-2-hydroxyglutarate (2HG) is not formed by wild-type IDH2. The production of R(−)-2-hydroxyglutarate (2HG) is believed to contribute to the formation and progression of cancer (Dang, L et al, Nature 2009, 462:739-44). The inhibition of mutant IDH1 and/or mutant IDH2 and their neoactivity is therefore a potential therapeutic treatment for cancer.

Vorasidenib (AG-881) is an orally available, brain penetrant second-generation dual mutant isocitrate dehydrogenase 1 and 2 (mIDH1/2) inhibitor currently undergoing clinical trials for the treatment of glioma, including low grade glioma.

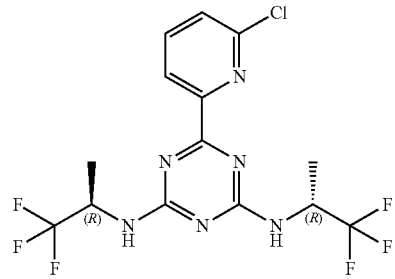

Vorasidenib (AG-881)

Vorasidenib (AG-881) is described in U.S. Pat. No. 9,579,324, which is incorporated herein by reference as though fully set forth. There is a need to identify potential biologically active vorasidenib metabolites that persist in the human body upon vorasidenib dosing in order to better understand the clinical activity of vorasidenib and to provide potential novel inhibitors of mutant IDH1/IDH2.

SUMMARY OF INVENTION

Described herein are Compounds 1 to 7 (e.g., Compound 1, Compound 2, Compound 3, Compound 4, Compound 5, Compound 6 and Compound 7), and pharmaceutically acceptable salts thereof:

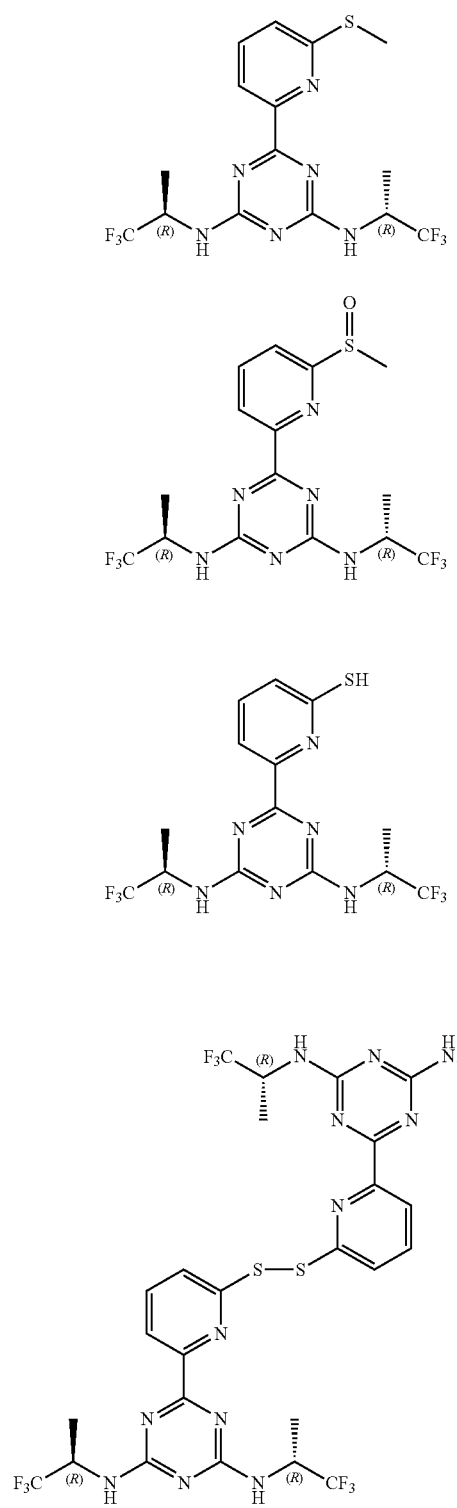

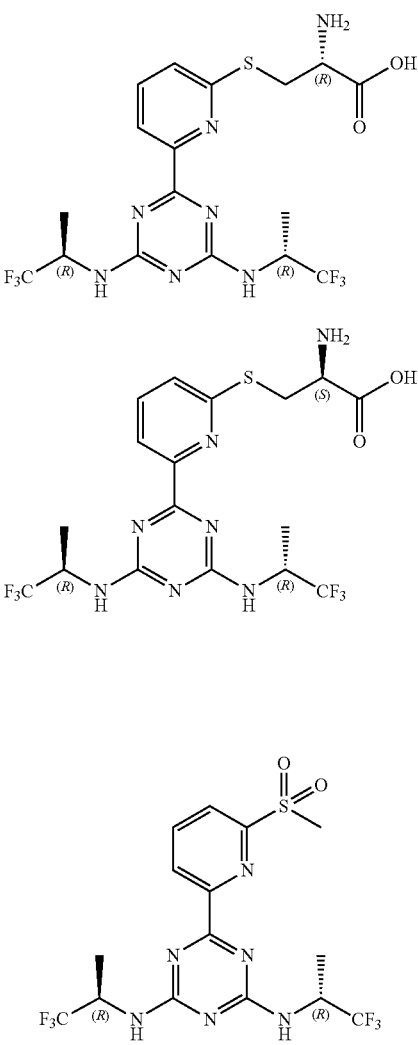

The compounds selected from Compounds 1 to 7, or pharmaceutical salts thereof, or as described in any one of the embodiments herein inhibits at least one of mutant IDH1 or mutant IDH2. Also described herein are pharmaceutical compositions comprising a compound selected from Compounds 1 to 7 or a pharmaceutical salt thereof and methods of using such compositions to treat cancers characterized by the presence of at least one of mutant IDH1 or mutant IDH2.

In one embodiment, the compound is

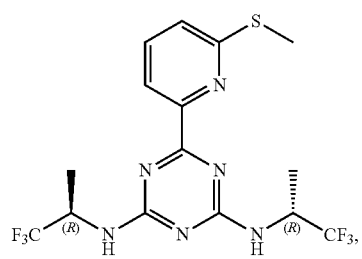

or a pharmaceutically acceptable salt thereof, in a purified form.

In one embodiment, the compound is

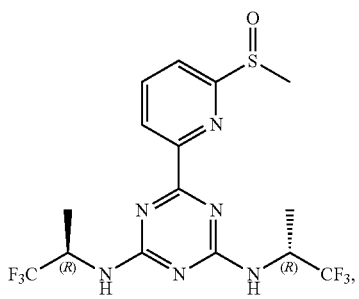

or a pharmaceutically acceptable salt thereof, in a purified form.

In one embodiment, the compound is

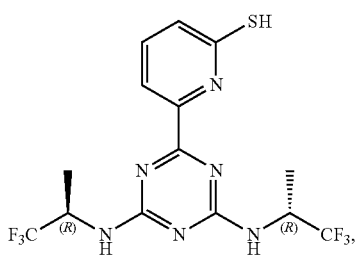

or a pharmaceutically acceptable salt thereof, in a purified form.

In one embodiment, the compound is

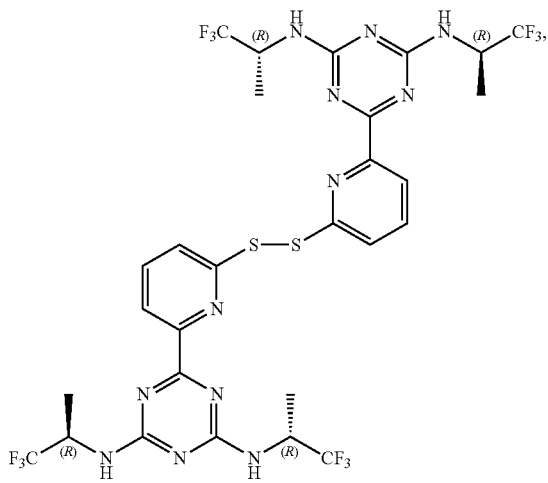

or a pharmaceutically acceptable salt thereof, in a purified form.

In one embodiment, the compound is

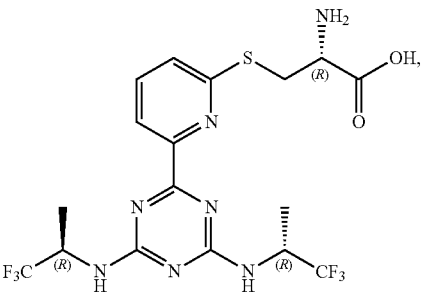

or a pharmaceutically acceptable salt thereof, in a purified form.

In one embodiment, the compound is

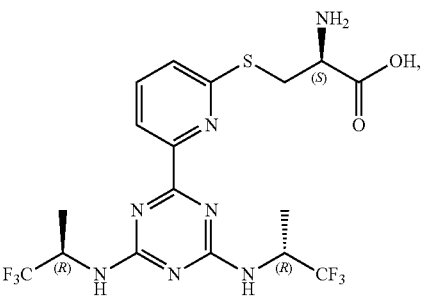

or a pharmaceutically acceptable salt thereof, in a purified form.

In one embodiment, the compound is

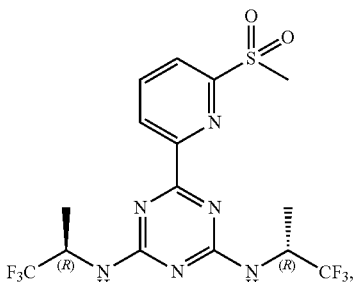

or a pharmaceutically acceptable salt thereof, in a purified form.

In one aspect, the invention provides a pharmaceutical composition comprising one or more compounds selected from Compounds 1 to 7, or a pharmaceutically acceptable salt thereof, and one or more pharmaceutically acceptable excipients.

In one embodiment, the pharmaceutical composition comprises

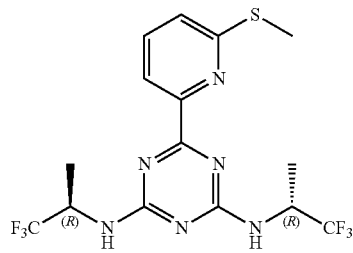

or a pharmaceutically acceptable salt thereof.

In one embodiment, the pharmaceutical composition comprises

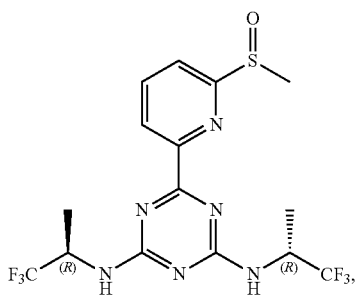

or a pharmaceutically acceptable salt thereof.

In one embodiment, the pharmaceutical composition comprises

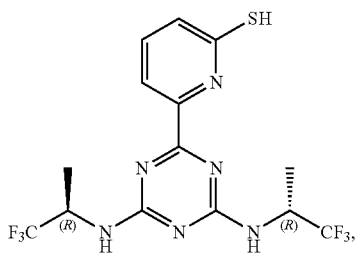

or a pharmaceutically acceptable salt thereof.

In one embodiment, the pharmaceutical composition comprises

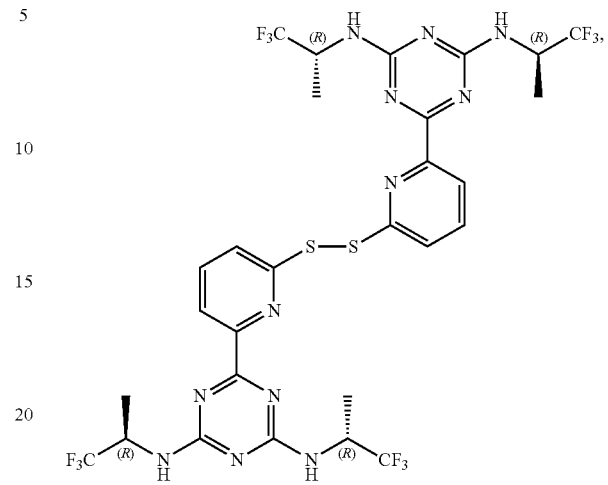

or a pharmaceutically acceptable salt thereof.

In one embodiment, the pharmaceutical composition comprises

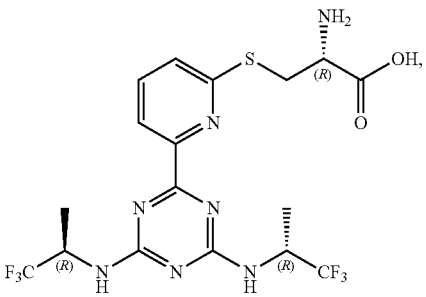

or a pharmaceutically acceptable salt thereof.

In one embodiment, the pharmaceutical composition comprises

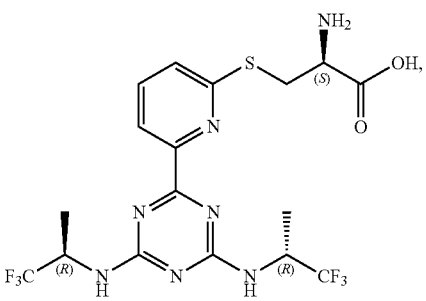

or a pharmaceutically acceptable salt thereof.

In one embodiment, the pharmaceutical composition comprises

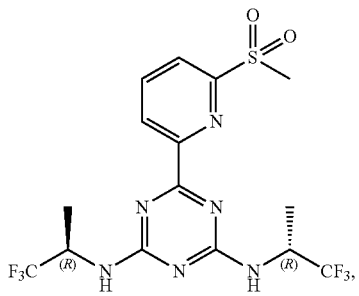

or a pharmaceutically acceptable salt thereof.

In one aspect, the invention provides a method of treating a cancer comprising administering to a patient in need thereof a therapeutically effective amount of one or more compounds selected from purified Compounds 1 to 7 or a pharmaceutically acceptable salt thereof, wherein the cancer is characterized by the presence of at least one mutation chosen from an IDH1 mutation or an IDH2 mutation.

In one embodiment, the method comprises administering to the patient a therapeutically effective amount of purified

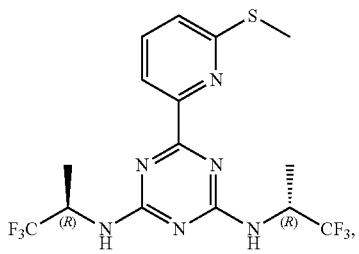

or a pharmaceutically acceptable salt thereof.

In one embodiment, the method comprises administering to the patient a therapeutically effective amount of purified

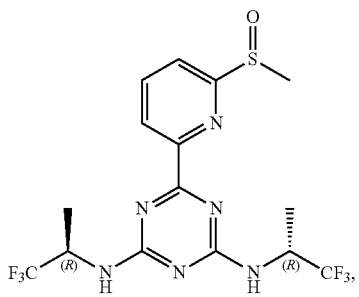

or a pharmaceutically acceptable salt thereof.

In one embodiment, the method comprises administering to the patient a therapeutically effective amount of purified

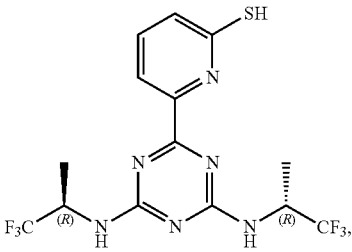

or a pharmaceutically acceptable salt thereof.

In one embodiment, the method comprises administering to the patient a therapeutically effective amount of purified

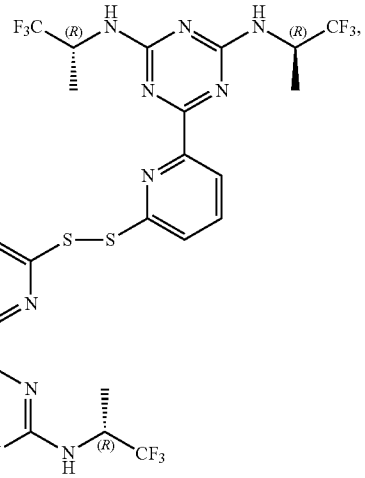

or a pharmaceutically acceptable salt thereof.

In one embodiment, the method comprises administering to the patient a therapeutically effective amount of purified

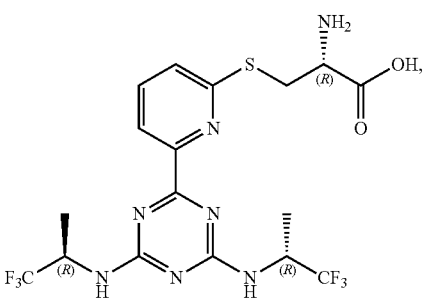

or a pharmaceutically acceptable salt thereof.

In one embodiment, the method comprises administering to the patient a therapeutically effective amount of purified

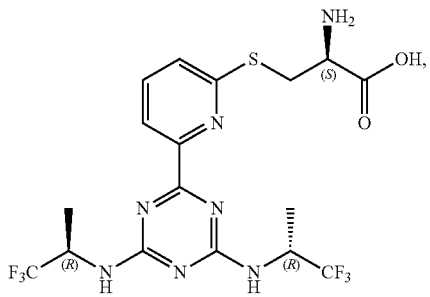

or a pharmaceutically acceptable salt thereof.

In one embodiment, the method comprises administering to the patient a therapeutically effective amount of purified

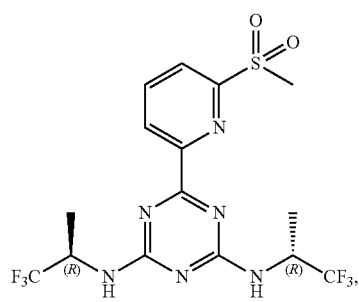

or a pharmaceutically acceptable salt thereof.

In one aspect, the invention provides a method of treating a cancer comprising administering to a patient in need thereof a therapeutically effective amount of a composition comprising one or more compounds selected from purified Compounds 1 to 7, or a pharmaceutically acceptable salt thereof, wherein the cancer is characterized by the presence of at least one mutation chosen from an IDH1 mutation or an IDH2 mutation.

In one embodiment of the methods described herein, the cancer is selected from glioma (including low grade glioma), glioblastoma (including secondary glioblastoma), grade II or III astrocytoma, grade II or III oligodendroglioma, acute myelogenous leukemia (AML), sarcoma, melanoma, non-small cell lung cancer (NSCLC), cholangiocarcinomas, chondrosarcoma, myelodysplastic syndromes (MDS), myeloproliferative neoplasm (MPN), colon cancer, and angio-immunoblastic non-Hodgkin's lymphoma (NHL) in a patient.

In one embodiment of the methods described herein, the cancer is glioma. In a further embodiment, the glioma is a low grade glioma or a high grade glioma.

In one embodiment, provided is a method of treating a glioma in a subject in need thereof comprising administering to the subject a therapeutically effective amount of one or more compounds selected from purified Compounds 1 to 7, or a pharmaceutically acceptable salt thereof.

In one embodiment, the method of treating glioma comprises administering to a subject in need thereof a therapeutically effective amount of purified:

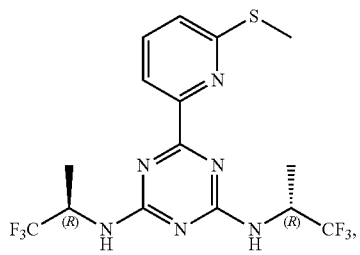

or a pharmaceutically acceptable salt thereof.

In one embodiment, the method of treating glioma comprises administering to a subject in need thereof a therapeutically effective amount of purified:

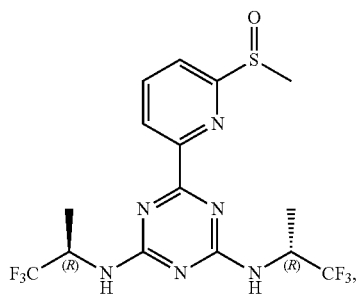

or a pharmaceutically acceptable salt thereof.

In one embodiment, the method of treating glioma comprises administering to a subject in need thereof a therapeutically effective amount of purified:

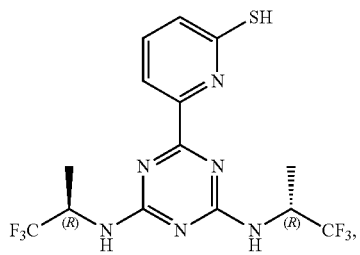

or a pharmaceutically acceptable salt thereof.

In one embodiment, the method of treating glioma comprises administering to a subject in need thereof a therapeutically effective amount of purified:

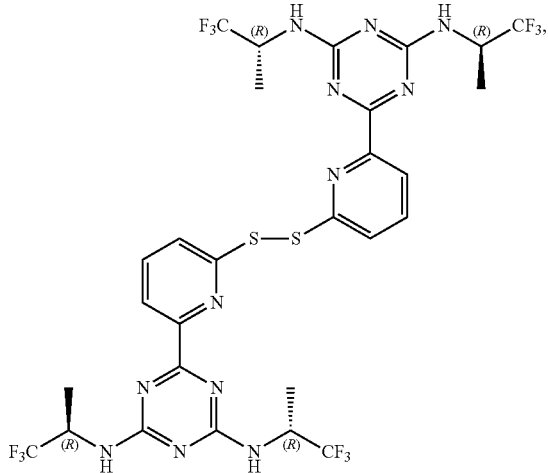

or a pharmaceutically acceptable salt thereof.

In one embodiment, the method of treating glioma comprises administering to a subject in need thereof a therapeutically effective amount of purified:

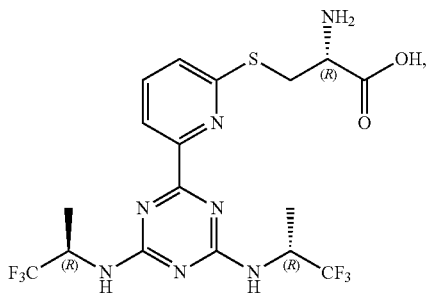

or a pharmaceutically acceptable salt thereof.

In one embodiment, the method of treating glioma comprises administering to a subject in need thereof a therapeutically effective amount of purified:

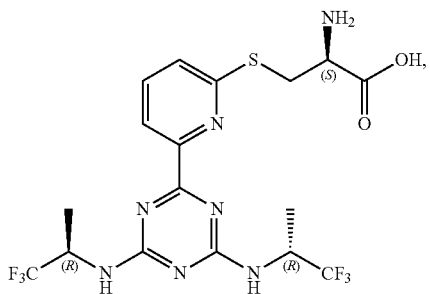

or a pharmaceutically acceptable salt thereof.

In one embodiment, the method of treating glioma comprises administering to a subject in need thereof a therapeutically effective amount of purified:

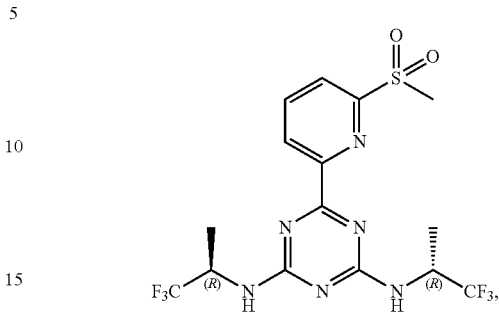

or a pharmaceutically acceptable salt thereof.

In one embodiment, provided is a method of treating a glioma comprising administering to a patient in need thereof a therapeutically effective amount of a composition comprising one or more compounds selected from Compounds 1 to 7, or a pharmaceutically acceptable salt thereof, wherein the glioma is characterized by the presence of at least one mutation chosen from an IDH1 mutation or an IDH2 mutation.

In one embodiment, provided is a method of treating low grade glioma comprising administering to a patient in need thereof a therapeutically effective amount of a composition comprising one or more compounds selected from Compounds 1 to 7, or a pharmaceutically acceptable salt thereof, wherein the glioma is characterized by the presence of at least one mutation chosen from an IDH1 mutation or an IDH2 mutation.

In one embodiment of the methods for treating glioma described herein, the glioma is characterized by the presence of at least one mutation selected from an IDH1 mutation and an IDH2 mutation.

In certain embodiments, the mutation is an IDH1 mutation. In some embodiments, the IDH1 mutation is an R132X mutation. In further embodiments, the IDH1 mutation is an R132H or R132C mutation.

In some embodiments, the mutation is an IDH2 mutation. In further embodiments, the mutation is a R140X or R172X mutation. In certain embodiments, the mutation is a R140Q, R140W, or an R140L mutation. In other embodiments, the mutation is an R172K or R172G mutation.

In some embodiments of the methods described herein, the amount of the compound or pharmaceutically acceptable salt thereof administered to the patient is between 1 and 5000 mg/day. In certain embodiments, the amount of the compound or pharmaceutically acceptable salt thereof administered to the patient is between 1 and 2000 mg/day. In certain embodiments, the amount of the compound or pharmaceutically acceptable salt thereof administered to the patient is between 1 and 1000 mg/day. In some embodiments, the amount of compound or pharmaceutically acceptable salt thereof administered to the patient is between 1 and 500 mg/day.

In certain embodiments of the methods described herein, the compound or composition is administered orally.

In certain embodiments of the methods described herein, the compound or composition is administered in combination with an additional therapeutic modality. In certain embodiments, the additional therapeutic modality is selected from radiation, surgical resection, anti-cancer medications, anti-epileptic medications, anti-seizure medications and anti-emesis medications.

In some embodiments, the anti-cancer medications are selected from chemotherapy with cytotoxic or cytostatic agents, targeted medications, antibody therapy, immunotherapy and hormonal therapy.

BRIEF DESCRIPTION OF THE DRAWINGS

FIG. 1 Represents a number of proposed theoretical biotransformation pathways of AG-881 (ivosidenib) in humans.

DETAILED DESCRIPTION

The details of the construction and the arrangement of components set forth in the following description or illustrated in the drawings are not meant to be limiting. Other embodiments and different ways to practice the subject matter of this application are expressly included. Also, the phraseology and terminology used herein is for the purpose of description and should not be regarded as limiting. The use of "including," "comprising," or "having," "containing," "involving", and variations thereof herein, is meant to encompass the items listed thereafter and equivalents thereof as well as additional items.

Definitions

The term "bodily fluid" includes one or more of amniotic fluid surrounding a fetus, aqueous humour, blood (e.g., whole blood or blood plasma), cerebrospinal fluid, cerumen, chyme, Cowper's fluid, feces, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, the term "daily dose" represents the total amount of therapeutic agent to be administered in any 24 hour period, and is used interchangeably with "amount/day". By way of example, "a daily dose of 100 mg," or "a dose of 100 mg/day," or "an amount of 100 mg/day" refer to administering to the patient a total of 100 mg of the therapeutic agent in any 24 hour period. The daily dose can be administered once a day (i.e., QD, or once daily or every 24 hours) or fractionated into multiple doses to be administered at different times in a 24 hour period (e.g., BID or twice daily or every 12 hours; TD or three times daily or every 8 hours; QID or four times daily or every 6 hours, etc.). Each of the doses (e.g., the daily dose or the fractionated doses) can be administered as a single dosage form (e.g., a single tablet or capsule) or as multiple dosage forms (e.g., two or more tablets or capsules). By the way of example, a daily dose of 1000 mg (i.e., a dose of 1000 mg/day) administered BID (i.e., twice daily) can be administered as, for instance, two dosage forms (e.g., capsules or tablets), each containing 250 mg therapeutic agent (e.g., a compound selected from purified Compounds 1 to 7 or a pharmaceutically acceptable salt thereof) every 12 hours.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. In some embodiments the human patient is a child (defined as a person that is less than 18 years old). In other embodiments the human patient is an adult (defined as a person this is equal to or greater than 18 years old). The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, the terms "purified," "in purified form" or "in isolated and purified form" in connection with a compound refers to the physical state of said compound after being physically separated from a synthetic process (e.g., from a reaction mixture), natural source, or from a bodily fluid or a combination thereof and/or being subjected to a purification process or processes. The "purification process or processes" referred to above are either described herein or are well known to the skilled artisan (e.g., chromatography, recrystallization and the like), and the purity of the compounds obtained by such purification process or processes is determined by standard analytical techniques described herein or are well known to the skilled artisan. In some embodiments, a purified compound does not have to be physically separated from a reaction mixture or bodily fluid prior to purification, e.g., the reaction mixture or bodily fluid is subjected to the purification process and the desired compound is isolated in purified form after completion of the purification process. In further embodiments, a compound may be optionally subjected to multiple purification processes. As examples, the purification techniques disclosed herein result in isolated and purified forms of the subject Compounds 1 to 7. Such isolation and purification techniques would be expected to result in compound purities of about 90 wt % or better (e.g., over 90 wt %, over 95 wt %, over 97 wt %, over 98 wt % or over 99 wt % purity).

Compounds

Provided are Compounds 1 to 7, or pharmaceutically acceptable salts or hydrates thereof:

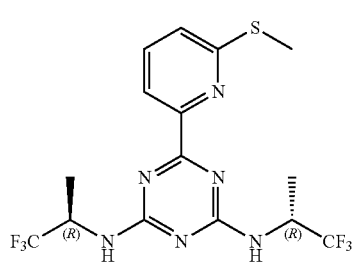

1

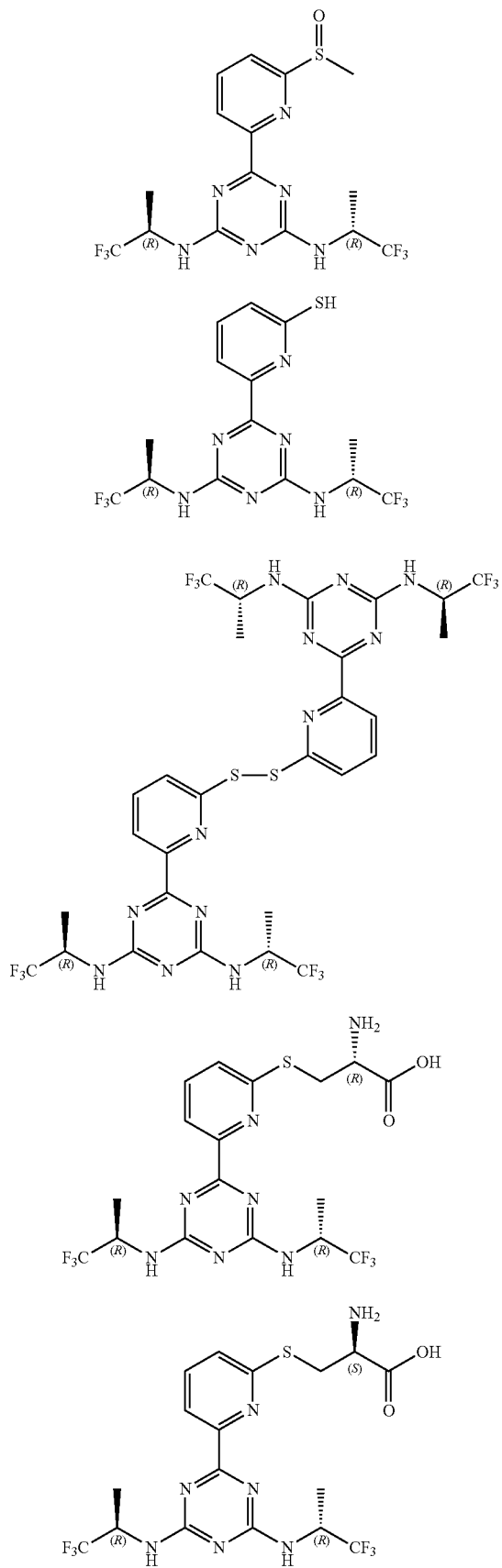

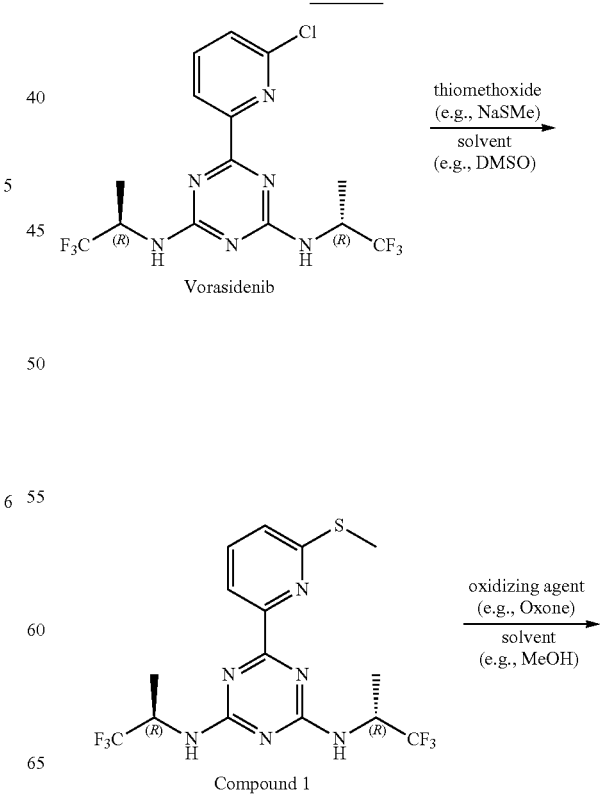

Compounds 1 to 7 are observed in one or more bodily fluids or are proposed metabolites that can be obtained upon oral dosing of vorasidenib (AG-881) in humans or synthesized de novo. A study to profile and identify vorasidenib and its metabolites in selected plasma, urine and feces samples collected from human subjects after a single oral dose of [$^{14}$C]AG-881 and concomitant intravenous microdose of [$^{13}$C$_3$ $^{15}$N$_3$]AG-881 is described in Example 8.

Compounds 1 to 7 can be synthetically prepared from commercially available materials using methods and combinations of methods known in the art. Exemplary methods for the synthesis of Compounds 1 to 7 are described in Examples 1-7.

For instance, Compound 1 and Compound 2 can be prepared from 6-(6-chloropyridin-2-yl)-N2, N4-bis((R)-1,1,1-trifluoropropan-2-yl)-1,3,5-triazine-2,4-diamine (Vorasidenib, AG-881) according to Scheme 1.

19
-continued

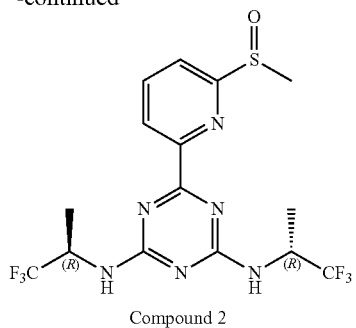

Compound 2

Treatment of Vorasidenib with a thiomethoxide (e.g., sodium thiomethoxide) in a suitable organic solvent (e.g., a polar, aprotic organic solvent, e.g., dimethylsulfoxide) results in the formation of Compound 1. The reaction can take place at temperatures between 0 and 30° C. and can optionally be conducted under an inert atmosphere (e.g., under a nitrogen atmosphere).

Further, Compound 2 can be synthetically prepared from Compound 1 by oxidation with an oxidizing agent (e.g., Oxone) in a suitable organic solvent (e.g., a polar organic solvent, e.g., a polar protic organic solvent, e.g., methanol).

Compounds 3, 4, 5 and 6 can be prepared from Vorasidenib (AG-881) by methods generally depicted in Scheme 2

Scheme 2

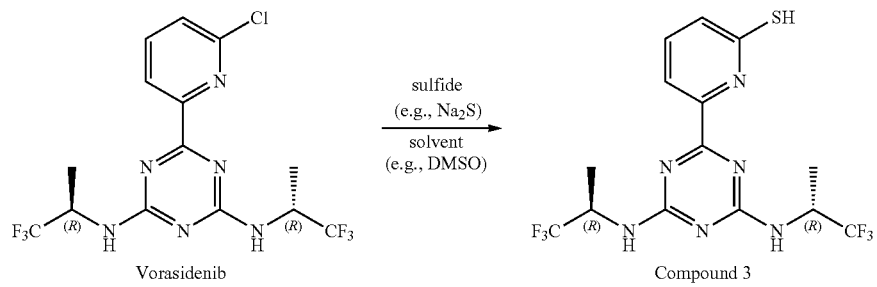

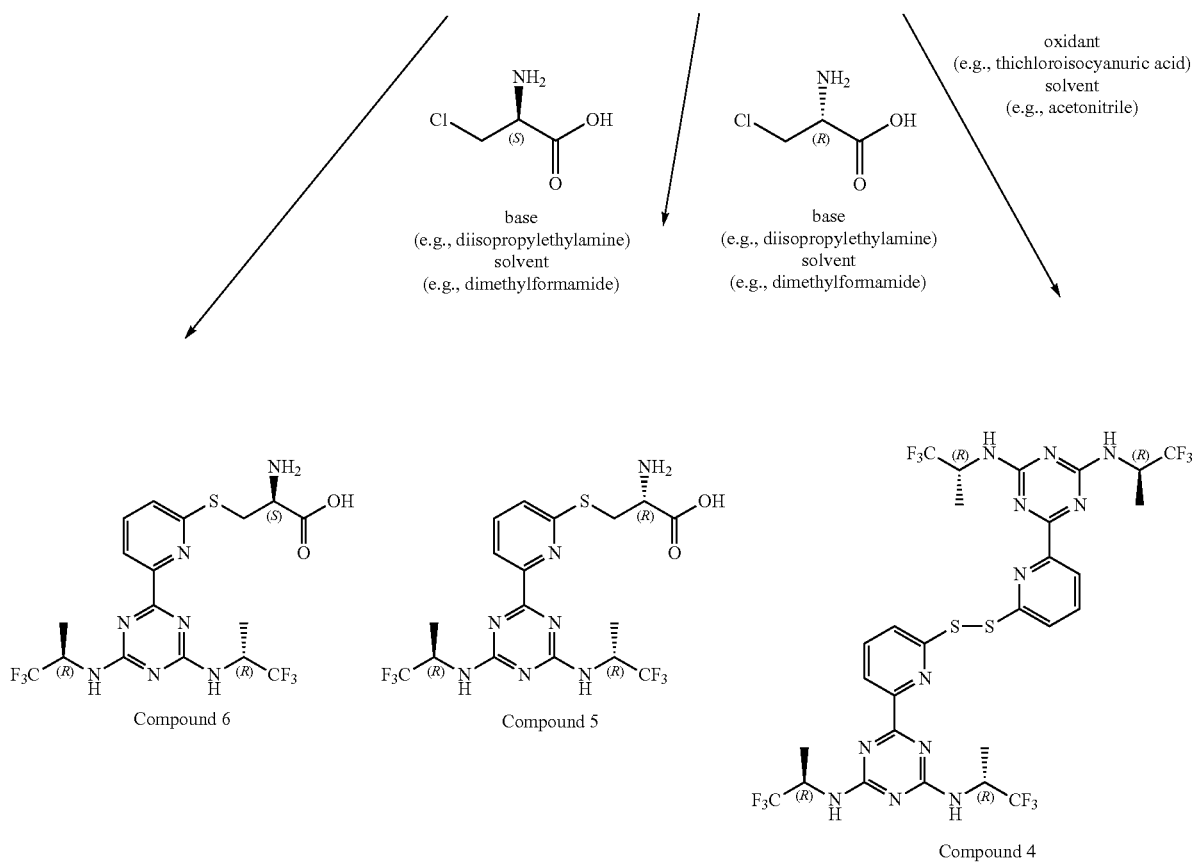

Vorasidenib (AG-881) can be dissolved in a suitable organic solvent (e.g., a polar, aprotic organic solvent, e.g., dimethylsulfoxide) and treated with a sulfide reagent (e.g., sodium sulfide) to provide Compound 3. The reaction can take place at temperatures between 0 and 30° C. and can optionally be conducted under an inert atmosphere (e.g., under a nitrogen atmosphere). Compound 4 can in turn be obtained by treating Compound 3 with an oxidizing agent (e.g., trichloroisocyanuric acid) in an organic solvent (e.g., a polar aprotic organic solvent, e.g., acetonitrile). The reaction can take place at temperatures between −40° C. and 0° C. (e.g., −20° C.) and can optionally be conducted under an inert atmosphere (e.g., under a nitrogen atmosphere). Compounds 5 and 6 can be obtained by treating Compound 3 with the appropriate enantiopure 2-amino-3-chloropropanoic acid in an organic solvent (e.g., a polar, aprotic organic solvent, e.g., N,N-Dimethylformamide) in the presence of a base (e.g., an organic amine base, e.g., N, N-Diisopropyiethylamine). The reaction can take place at temperatures between 20° C. and 100° C. (e.g., between 40° C. and 80° C., e.g., around 60° C.). In some embodiments, the reaction can be conducted under an inert atmosphere (e.g., under a nitrogen atmosphere).

Compound 7 can be prepared from Vorasidenib (AG-881) by methods generally depicted in Scheme 3.

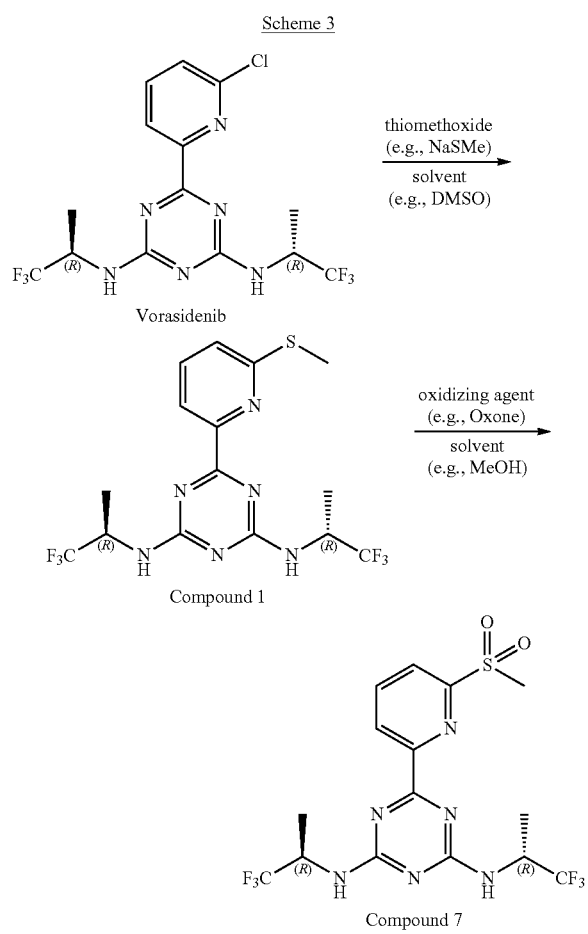

Treatment of Vorasidenib with a thiomethoxide (e.g., sodium thiomethoxide) in a suitable organic solvent (e.g., a polar, aprotic organic solvent, e.g., dimethylsulfoxide) results in the formation of Compound 1. The reaction can take place at temperatures between 0 and 30° C. and can optionally be conducted under an inert atmosphere (e.g., under a nitrogen atmosphere).

Further, Compound 7 can be synthetically prepared from Compound 1 by oxidation with an oxidizing agent (e.g., Oxone) in a suitable organic solvent (e.g., a polar organic solvent, e.g., a polar protic organic solvent, e.g., methanol) in the presence of water.

Compounds 1 to 7 contain one or more asymmetric centers and thus may occur or be isolated or synthesized as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, Compounds 1 to 7 are enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

Compounds 1 to 7 may also be prepared with one or more isotopic substitutions. For example, H may be in any isotopic form, including $^1$H, $^2$H (D or deuterium), and $^3$H (T or tritium); C may be in any isotopic form, including $^{11}$C, $^{12}$C, $^{13}$C, and $^{14}$C; N may be in any isotopic form, including $^{13}$N, $^{14}$N and $^{15}$N; O may be in any isotopic form, including $^{15}$O, $^{16}$O and $^{18}$O; F may be in any isotopic form, including 18F; and the like. For example, the compound is enriched in a specific isotopic form of H, C, N, O and/or F by at least about 60%, 65%, 70%, 75%, 80%, 85%, 90%, 95%, 96%, 97%, 98%, or 99%. Certain isotopically-labelled compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds can generally be prepared by procedures analogous to those disclosed in the Examples, by substituting an appropriate isotopically labelled reagent for a non-isotopically labelled reagent.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e., $NH^{4+}$) and substituted ammonium ions (e.g., $NH_3R^+$, $NH_2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Mesylates of each compound in Table 1 are explicitly included herein. Examples of suitable polymeric organic anions include, but are not limited to, those derived from the following polymeric acids: tannic acid, carboxymethyl cellulose.

The compounds provided herein therefore include the compounds themselves, as well as their salts, hydrates and their prodrugs, if applicable. The compounds provided herein may be modified and converted to prodrugs by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds. Calcium and sodium phosphates of each one of Compounds 1 to 7, if applicable, are explicitly included herein. Amino acid (e.g., valine) esters of each one of Compounds 1 to 7, if applicable, are explicitly included herein.

Compositions and Routes of Administration

The compounds utilized in the methods described herein may be formulated together with a pharmaceutically acceptable carrier or adjuvant into pharmaceutically acceptable compositions prior to be administered to a subject. In one embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In certain embodiments, any one of Compounds 1 to 7 or a pharmaceutically acceptable salt thereof is administered in compositions comprising one of the compounds described herein (e.g., one or more of Compounds 1 to 7) or a pharmaceutically acceptable salt thereof and one or more polymer(s) as part of a solid dispersion (e.g., an amorphous solid dispersion). In some embodiments, the solid dispersion comprises a compound selected from Compounds 1 to 7 or a pharmaceutically acceptable salt thereof, and one or more polymer(s). In some embodiments, the solid dispersion comprises one of Compounds 1 to 7 or a pharmaceutically acceptable salt thereof, one or more polymer(s), and one or more surfactant(s). In some embodiments, the solid dispersion comprises one of Compounds 1 to 7, or a pharmaceutically acceptable salt thereof and one polymer. In some embodiments, the solid dispersion comprises one of Compounds 1 to 7 or a pharmaceutically acceptable salt thereof, one polymer, and a surfactant.

In some embodiments, at least a portion of the active ingredient (e.g., one of Compounds 1 to 7 or a pharmaceutically acceptable salt thereof), in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline compound.

In some embodiments, the composition is an amorphous solid (e.g., spray dried) dispersion comprising one of Compounds 1 to 7 or a pharmaceutically acceptable salt thereof, and a polymer. The amorphous solid dispersion can include, e.g., less than about 30%, less than about 20%, less than about 15%, less than about 10%, less than about 5%, less than about 4%, less than about 3%, less than about 2%, or less than about 1% of crystalline compound, (e.g., be substantially free of a crystalline compound selected from Compounds 1 to 7 or a pharmaceutically acceptable salt thereof).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hypromellose acetate succinate, (HPMCAS), hydroxypropylcellulose (HPC)), ethylcellulose, or cellulose acetate phthalate); polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit.RTM. E); cyclodextrins (e.g., .beta.-cyclodextrin); Poly(D, L-lactide) (PLA), Poly(D,L-lactide, co-glycolide acid (PLGA); and copolymers and derivatives thereof, including for example polyvinylpyrrolidone-vinyl acetate (PVP-VA), Polyvinyl caprolactam-polyvinyl, and acetate-polyethyleneglycol copolymer, Methylacrylate/methacrylic acid copolymer, Soluplus; Copovidone; and mixtures thereof.

In some embodiments, the solid dispersion includes at least one water-soluble polymer. In some embodiments, the solid dispersion includes at least one partially water-soluble polymer. In some embodiments, the polymer is a cellulose derivative polymer. In other embodiments, the polymer is copovidone. In still other embodiments, the polymer is a cyclodextrin. In some embodiments, the solid dispersion includes more than one polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP)), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer (s) is polyvinylpyrrolidone (PVP).

In some embodiments, the compound (e.g., a compound selected from Compounds 1 to 7) or a pharmaceutically acceptable salt thereof, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the compound (e.g., a compound selected from Compounds 1 to 7) or a pharmaceutically acceptable salt thereof, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In the above embodiments, the remainder of the weight of the composition is represented by one or more polymers. In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w, such that the sum of the weights of active ingredient (e.g., compound selected from Compounds 1 to 7 or a pharmaceutically acceptable salt thereof), polymer and surfactant is 100%.

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising a compound selected from Compounds 1 to 7 or a pharmaceutically acceptable salt thereof, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In one embodiment, the spray-drying is fluidized spray drying (FSD).

In certain embodiments, the process for preparing a solid dispersion of a compound selected from Compounds 1 to 7 or a pharmaceutically acceptable salt thereof comprises:
 a) forming a mixture of a Compound (e.g., a compound selected from Compounds 1 to 7) or a pharmaceutically acceptable salt thereof a polymer, and a solvent; and
 b) spray-drying the mixture to form a solid dispersion comprising Compound and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein or as determined by one of skill in the art.

In certain embodiments, the pharmaceutical compositions comprising a solid dispersion may be made by a process described herein. For example, pharmaceutical composition can comprise solid dispersion of: (a) a Compound selected from Compounds 1 to 7 or a pharmaceutically acceptable salt thereof and (b) one or more polymer(s), and optionally one or more surfactant(s) and optionally one or more additional excipient(s).

The pharmaceutical compositions disclosed herein may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

In some embodiments, the Compound selected from Compounds 1 to 7, or a pharmaceutically acceptable salt thereof, is orally administered in an amount of from 1 to 5000 mg/day (e.g., 1 to 1000 mg/day, 1000-2000 mg/day, 2000-3000 mg/day, 3000-4000 mg/day or 4000-5000 mg/day). In one embodiment, the compound is administered in an amount from 1-1000 mg/day (e.g., 1-500 mg/day, 500-1000 mg/day). In one embodiment, the compound is administered in an amount from 1-500 mg/day (e.g., 1-100 mg/day, 100-200 mg/day, 200-300 mg/day, 300-400 mg/day, 400-500 mg/day). In one embodiment, the compound is administered in an amount from 500-1000 mg/day (e.g., 500-750 mg/day, 750-1000 mg/day). In one embodiment, the compound is administered in an amount from 1000-2000 mg/day (e.g., 1000-1500 mg/day, 1500-2000 mg/day). In one embodiment, the compound is administered in an amount from 2000-3000 mg/day (e.g., 2000-2500 mg/day, 2500-3000 mg/day). In one embodiment, the compound is administered in an amount from 3000-4000 mg/day (e.g., 3000-3500 mg/day, 3500-4000 mg/day). In one embodiment, the compound is administered in an amount from 4000-5000 mg/day (e.g., 4000-4500 mg/day, 4500-5000 mg/day). In some embodiments, the compound selected from Compounds 1 to 7, or a pharmaceutically acceptable salt thereof, is orally administered in an amount of from 1 to 500 mg/day, 1 to 250 mg/day, 5 to 100 mg/day, 8 to 75 mg/day, 10 to 50 mg/day, 15 to 40 mg/day, 20 to 30 mg/day, or about 25 mg/day. In some embodiments, the compound selected from Compounds 1 to 7, or a pharmaceutically acceptable salt thereof, is orally administered in an amount of from 1 to 500 mg/day, 10 to 250 mg/day, 20 to 100 mg/day, 30 to 80 mg/day, 40 to 60 mg/day, 45 to 55 mg/day, or about 50 mg/day. In some embodiments, the compound selected from Compounds 1 to 7, or a pharmaceutically acceptable salt thereof, is orally administered in an amount of from 1 to 500 mg/day, 20 to 400 mg/day, 40 to 200 mg/day, 50 to 150 mg/day, 75 to 125 mg/day, 85 to 115 mg/day, 90 to 110 mg/day, or about 100 mg/day. In some embodiments, the compound selected from Compounds 1 to 7, or a pharmaceutically acceptable salt thereof, is orally administered in an amount of from 1 to 500 mg/day, 50 to 400 mg/day, 100 to 300 mg/day, 150 to 250 mg/day, 175 to 225 mg/day, 185 to 215 mg/day, 190 to 210 mg/day, or about 200 mg/day. In some embodiments, the compound selected from Compounds 1 to 7, or a pharmaceutically acceptable salt thereof, is orally administered in an amount of from 1 to 500 mg/day, 100 to 500 mg/day, 200 to 400 mg/day, 250 to 350 mg/day, 275 to 375 mg/day, 285 to 315 mg/day, 290 to 310 mg/day, or about 300 mg/day. In some embodiments, a daily dose of a compound selected from Compounds 1 to 7, or a pharmaceutically acceptable salt thereof, is administered at one time (i.e., administered in a single dosage form) or in one or more divided doses (i.e., administered in two or more dosage forms) over a twenty-four (24) period. In some embodiments, the daily dose or each of the divided doses may be administered as a single dosage form or as multiple dosage forms (e.g., administering two or more dosage forms at the time of each administration) to facilitate administration and patient compliance. In some embodiments the dosage forms are tablets. In other embodiments the dosage forms are capsules.

In other embodiments, a compound disclosed herein (e.g., a Compound selected from Compounds 1 to 7), or a pharmaceutically acceptable salt thereof, is administered once per day in an amount of about 1 mg, of about 5 mg, of about 10 mg, about 25 mg, about 50 mg, about 100 mg, about 200 mg about 300 mg, about 400 mg, about 500 mg, about 750 mg, about 1000 mg, about 1250 mg, about 1500 mg, about 2000 mg, about 2500 mg, about 3000 mg, about 3500 mg, about 4000 mg or about 5000 mg per administration.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

The pharmaceutical compositions described herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Alternatively, the compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound selected from Compounds 1 to 7, or a pharmaceutically acceptable salt thereof, or a compound described in any one of the embodiments herein, may further comprise another therapeutic agent useful for treating cancer.

When the compositions of the present disclosure comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

Methods of Use

Provided is a method for inhibiting mutant IDH1 and/or mutant IDH2 activity comprising contacting a subject in need thereof with a compound selected from Compounds 1 to 7 or a pharmaceutically acceptable salt thereof.

Also provided are methods of treating a cancer characterized by the presence of a mutant allele of IDH1 comprising the step of administering to subject in need thereof (a) a compound of the present disclosure (e.g., a Compound selected from Compounds 1 to 7) or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation results in a new ability of the enzyme to catalyze the NADPH-dependent reduction of α-ketoglutarate to R(−)-2-(2HG) in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132 H or R132C. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NADPH-dependent reduction of α-ketoglutarate to R(−)-2-hydroxyglutarate (2HG), and in particular R132H mutations of IDH1, characterize a subset of all types of cancers, without regard to their cellular nature or location in the body. Thus, the compounds and methods of this disclosure are useful to treat any type of cancer that is characterized by the presence of a mutant allele of IDH1 imparting such activity and in particular an IDH1 R132H or R132C mutation.

In one embodiment the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

IDH1 R132X mutations are known to occur in certain types of cancers as indicated in Table 1, below.

TABLE 1

IDH mutations associated with certain cancers

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in gliomas (including low grade glioma), glioblastoma (including secondary glioblastoma), acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (including low grade glioma), glioblastoma (including secondary glioblastoma), grade II and III astrocytomas, grade II and III oligodendrogliomas, acute myelogenous leukemia, sarcoma, melanoma, non-small cell lung cancer (NSCLC), cholangiocarcinomas, chondrosarcoma, myelodysplastic syndromes (MDS), myeloproliferative neoplasm (MPN), colon cancer, or angio-immunoblastic non-Hodgkin's lymphoma (NHL) in a patient.

In another embodiment, the methods described herein are used to treat glioma (including low grade glioma), glioblastoma (including secondary glioblastoma), grade II and III astrocytomas, grade II and III oligodendrogliomas, acute myelogenous leukemia, sarcoma, melanoma, non-small cell lung cancer (NSCLC), cholangiocarcinomas (e.g., intrahepatic cholangiocarcinoma (IHCC)), chondrosarcoma, myelodysplastic syndromes (MDS), myeloproliferative neoplasm (MPN), prostate cancer, chronic myelomonocytic leukemia (CMML), B-acute lymphoblastic leukemias (B-ALL), B-acute lymphoblastic leukemias (B-ALL), myeloid sarcoma, multiple myeloma, lymphoma colon cancer, or angio-immunoblastic non-Hodgkin's lymphoma (NHL) in a patient.

In another embodiment, the methods described herein are used to treat advanced hematologic malignancies. In one embodiment, the advanced hematologic malignancy to be treated is lymphoma (e.g., Non-Hodgkin lymphoma (NHL) such B-cell lymphoma (e.g., Burkitt lymphoma, chronic lymphocytic leukemia/small lymphocytic lymphoma (CLlJSLL), diffuse large B-cell lymphoma, follicular lymphoma, immunoblastic large cell lymphoma, precursor B-lymphoblastic lymphoma, and mantle cell lymphoma) and T-cell lymphoma (e.g., mycosis fungoides, anaplastic large cell lymphoma, and precursor T-lymphoblastic lymphoma).

Accordingly, in one embodiment, the cancer is a cancer selected from any one of the cancer types listed in Table 1 or as further described herein, and the IDH R132X mutation is one or more of the IDH1 R132X mutations listed in Table1 for that particular cancer type.

Also provided is a method for inhibiting a mutant IDH2 activity comprising contacting a subject in need thereof with a compound of the present disclosure (e.g., a Compound selected from Compounds 1 to 7), or a pharmaceutically acceptable salt thereof.

Also provided are methods of treating a cancer characterized by the presence of a mutant allele of IDH2 comprising the step of administering to subject in need thereof (a) a compound of the disclosure (e.g., a Compound selected from Compounds 1 to 7), or a pharmaceutically acceptable salt thereof, or (b) a pharmaceutical composition comprising (a) and a pharmaceutically acceptable carrier.

In one embodiment, the cancer to be treated is characterized by a mutant allele of IDH2 wherein the IDH2 mutation results in a new ability of the enzyme to catalyze the NADPH-dependent reduction of α-ketoglutarate to R(−)-2-hydroxyglutarate (2HG) in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation results in a new ability of the enzyme to catalyze the NADPH-dependent reduction of α-ketoglutarate to R(−)-2-hydroxyglutarate (2HG), and in particular R140Q and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such activity and in particular an IDH2 R140Q and/or R172K mutation.

In one embodiment the cancer is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In another embodiment, one aspect of the invention provides a method of treating a cancer selected from glioma (including low grade glioma), glioblastoma (including secondary glioblastoma), grade II and III astrocytomas, grade II and III oligodendrogliomas myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma in a patient by administering to the patient a compound of the present disclosure (e.g., a Compound selected from Compounds 1 to 7) or a pharmaceutically acceptable salt thereof in an amount effective to treat the cancer. In a more specific embodiment, the cancer to be treated is glioma (including low grade glioma), glioblastoma (including secondary glioblastoma), grade II and III astrocytomas, grade II and III oligodendrogliomas myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL).

Treatment methods described herein can additionally comprise various evaluation steps prior to and/or following treatment with a compound of the present disclosure (e.g., a Compound selected from Compounds 1 to 7) or a pharmaceutically acceptable salt thereof.

In one embodiment, prior to and/or after treatment with a compound of the present disclosure (e.g., a Compound selected from Compounds 1 to 7) or a pharmaceutically acceptable salt thereof, the method further comprises the step of evaluating the growth, size, weight, invasiveness, stage and/or other phenotype of the cancer using one or more techniques known and used by those skilled in the art.

In one embodiment, prior to and/or after treatment with a compound of the present disclosure (e.g., a Compound selected from Compounds 1 to 7) or a pharmaceutically acceptable salt thereof, the method further comprises the step of evaluating the IDH1 or IDH2 genotype of the cancer. This may be achieved by ordinary methods in the art, such as DNA sequencing, immuno analysis, and/or evaluation of the presence, distribution or level of R(−)-2-hydroxyglutarate (2HG).

In one embodiment, prior to and/or after treatment with a compound of the present disclosure (e.g., a Compound selected from Compounds 1 to 7) or a pharmaceutically acceptable salt thereof, the method further comprises the step of determining the R(−)-2-hydroxyglutarate (2HG) level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one aspect of this embodiment, the efficacy of cancer treatment is monitored by measuring the levels of R(−)-2-hydroxyglutarate (2HG) in the subject. Typically, levels of R(−)-2-hydroxyglutarate (2HG) are measured prior to treatment, wherein an elevated level of R(−)-2-hydroxyglutarate (2HG) (together with confirmed IDH mutant status) is used to confirm eligibility for the use of a compound of the present disclosure (e.g., a Compound selected from Compounds 1 to 7) or a pharmaceutically acceptable salt thereof to treat the cancer. Once the elevated levels are established, the level of R(−)-2-hydroxyglutarate (2HG) is determined during the course of and/or following termination of treatment to establish target engagement (i.e., inhibition of mutant IDH by administration of a compound of the present disclosure or a pharmaceutically acceptable salt thereof). In certain embodiments, the level of R(−)-2-hydroxyglutarate (2HG) is only determined during the course of and/or following termination of treatment. A reduction of R(−)-2-hydroxyglutarate (2HG) levels during the course of treatment and following treatment is indicative of target engagement. Typically, R(−)-2-hydroxyglutarate (2HG) measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

R(−)-2-hydroxyglutarate (2HG) can be detected in a sample by LC/MS. The sample is mixed 80:20 with methanol and centrifuged at 3,000 rpm for 20 minutes at 4 degrees Celsius. The resulting supernatant can be collected and stored at −80 degrees Celsius prior to LC-MS/MS to assess 2-hydroxyglutarate (2HG) levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate (2HG), running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment the concentration of R(−)-2-hydroxyglutarate (2HG) is evaluated prior to treatment with a compound of the present disclosure (e.g., a Compound selected from Compounds 1 to 7) or a pharmaceutically acceptable salt thereof. In another embodiment the concentration of R(−)-2-hydroxyglutarate (2HG) is evaluated after treatment with a compound disclosed herein or a pharmaceutically acceptable salt thereof. In some embodiments the evaluation of R(−)-2-hydroxyglutarate (2HG) is performed using a biological fluid of a human patient. In other embodiments the evaluation of R(−)-2-hydroxyglutarate (2HG) is performed using biological material from a biopsy or tissue sample from a human patient. In some aspects the biopsy or tissue sample is from a brain tumor from a human patient. In some embodiments the biopsy or tissue sample is taken from the human patient before treatment with a compound of the present disclosure or after treatment with a compound of the present disclosure or both before and after treatment with a compound of the present disclosure.

In another embodiment a derivative of R(−)-2-hydroxyglutarate (2HG) formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of R(−)-2-hydroxyglutarate (2HG) is evaluated. Examples include species that build up or are elevated, or reduced, as a result of the presence of R(−)-2-hydroxyglutarate (2HG), such as glutarate or glutamate that will be correlated to R(−)-2-hydroxyglutarate (2HG), e.g., R-2HG.

Exemplary R(−)-2-hydroxyglutarate (2HG) derivatives include dehydrated derivatives such as the compounds provided below or a salt adduct thereof:

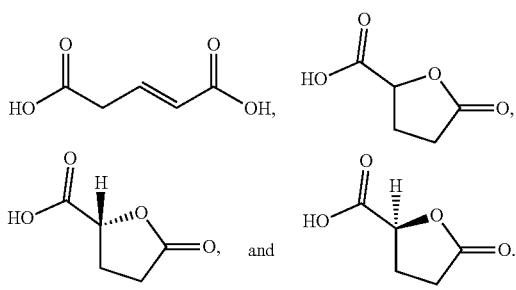

Also provided are methods of treating a disease selected from Maffucci syndrome and Ollier disease, characterized by the presence of a mutant allele of IDH1 comprising the step of administering to subject in need thereof (a) a compound of the present disclosure (e.g., a Compound selected from Compounds 1 to 7), or a pharmaceutically acceptable salt thereof, or (b) a pharmaceutical composition comprising (a) and a pharmaceutically acceptable carrier.

Brain Tumors Treated by Methods of the Invention

In one aspect, the methods of the invention are useful for treating brain tumors. This includes all tumors inside the human skull (cranium) or in the central spinal canal. The tumor may originate from the brain itself, but also from lymphatic tissue, blood vessels, the cranial nerves, the brain envelopes (meninges), skull, pituitary gland, or pineal gland. Within the brain itself, the involved cells may be neurons or glial cells (which include astrocytes, oligodendrocytes, and ependymal cells). Brain tumors may also spread from cancers primarily located in other organs (metastatic tumors).

In some embodiments, the brain tumor is a glioma, such as an ependymoma, astrocytoma, oligoastrocytoma, oligodendroglioma, ganglioglioma, glioblastoma (also known as glioblastoma multiforme), or mixed glioma. Gliomas are primary brain tumors and are classified into four grades (I, II, III, and IV) based on their appearance under a microscope, and particularly the presence of atypical cells, mitoses, endothelial proliferation, and necrosis. Grade I and II tumors, termed "low-grade gliomas," have none or one of these features and include diffuse astrocytomas, pilocytic astrocytomas, low-grade astrocytomas, low-grade oligoastrocytomas, low-grade oligodendrogliomas, gangliogliomas, dysembryoplastic neuroepithelial tumors, pleomorphic xanthoastrocytomas, and mixed gliomas. Grade III and IV tumors, termed "high-grade gliomas," have two or more of these features and include anaplastic astrocytomas, anaplastic oligodendrogliomas, anaplastic oligoastrocytomas, anaplastic ependymomas, and glioblastomas (including giant cell glioblastomas and gliosarcomas). In one aspect of these embodiments, the glioma is a low grade glioma. In another aspect of these embodiments, the glioma is a high grade glioma. In another aspect of these embodiments, the glioma is a glioblastoma(including secondary glioblastoma). In some embodiments, the brain tumor is a grade II or III astrocytoma. In some embodiments, the brain tumor is a grade II or III oligodendroglioma.

In further embodiments the brain tumor (e.g., glioma (including low grade glioma), glioblastoma (including secondary glioblastoma), grade II or III astrocytoma, grade II or III oligodendroglioma is newly diagnosed. In still further embodiments the brain tumor (e.g., glioma (including low grade glioma), glioblastoma (including secondary glioblastoma), grade II or III astrocytomas, grade II or III oligodendroglioma) has been pre-treated with one or more therapeutic modalities including surgery, radiation therapy, or one or more additional therapeutic agents. In other embodiments the brain tumor (e.g., glioma (including low grade glioma), glioblastoma (including secondary glioblastoma), grade II or III astrocytoma, grade II or III oligodendroglioma) has not been treated with radiation therapy.

In some embodiments, the brain tumor (e.g., glioma (including low grade glioma), glioblastoma (including secondary glioblastoma), grade II or III astrocytoma, grade II or III oligodendroglioma) to be treated is characterized by the presence of an IDH1 mutation, wherein the IDH1 mutation results in accumulation of R(−)-2-hydroxyglutarate (2HG) in a patient. In one aspect of these embodiments, the IDH1 mutation results in accumulation of R(−)-2-hydroxyglutarate (2HG) in a patient by providing a new ability of the enzyme to catalyze the NADPH-dependent reduction of α-ketoglutarate to R(−)-2-hydroxyglutarate (2HG) in a patient. In another aspect of these embodiments, the IDH1 mutation is an R132X mutation. In another aspect of these embodiments, the R132X mutation is selected from R132H, R132C, R132L, R132V, R132S and R132G. In another aspect of these embodiments, the R132X mutation is R132 H or R132C. In yet another aspect of these embodiments, the R132X mutation is R132H. In still another aspect of these embodiments, at least 30, 40, 50, 60, 70, 80 or 90% of the brain tumor (e.g., glioma (including low grade glioma), glioblastoma (including secondary glioblastoma), grade II or III astrocytoma, grade II or III oligodendroglioma) cells carry an IDH1 R132X mutation, such as an R132H, R132C, R132L, R132V, R132S or R132G mutation, at the time of diagnosis or treatment. A brain tumor (e.g., glioma (including low grade glioma), glioblastoma (including secondary glioblastoma), grade II or III astrocytoma, grade II or III oligodendroglioma) can be analyzed by sequencing cell samples to determine the presence and specific nature of (e.g., the changed amino acid present at) a mutation at amino acid 132 of IDH1.

In other embodiments, the brain tumor (e.g., glioma (including low grade glioma), glioblastoma (including secondary glioblastoma), grade II or III astrocytoma, grade II or III oligodendroglioma) to be treated is characterized by the presence of an IDH2 mutation, wherein the IDH2 mutation results in accumulation of R(−)-2-hydroxyglutarate (2HG) in a patient. In one aspect of these embodiments, the IDH2 mutation results in accumulation of R(−)-2-hydroxyglutarate (2HG) in a patient by providing a new ability of the enzyme to catalyze the NADPH dependent reduction of a ketoglutarate to R(−)-2-hydroxyglutarate (2HG) in a patient. In another aspect of these embodiments, the mutant IDH2 has an R140X mutation. In another aspect of these embodiments, the R140X mutation is a R140Q mutation. In another aspect of these embodiments, the R140X mutation is a R140W mutation. In another aspect of these embodiments, the R140X mutation is a R140L mutation. In another aspect of these embodiments, the mutant IDH2 has an R172X mutation. In another aspect of these embodiments, the R172X mutation is a R172K mutation. In another aspect of these embodiments, the R172X mutation is a R172G mutation. In still another aspect of these embodiments, at least 30, 40, 50, 60, 70, 80 or 90% of the brain tumor (e.g., glioma (including low grade glioma), glioblastoma (including secondary glioblastoma), grade II or III astrocytoma, grade II or III oligodendroglioma) cells carry an IDH2 R140X and/or R172X mutation, such as an R140Q, R140W, or R140L and/or R172K or R172G mutation, at the time of diagnosis or treatment. A brain tumor (e.g., glioma (including low grade glioma), glioblastoma (including secondary glioblastoma), grade II or III astrocytoma, grade II or III oligodendroglioma) can be analyzed by sequencing cell samples to determine the presence and specific nature of (e.g., the changed amino acid present at) a mutation at amino acid 140 and/or 172 of IDH2.

In still other embodiments, the brain tumor (e.g., glioma (including low grade glioma), glioblastoma (including secondary glioblastoma), grade II or III astrocytoma, grade II or III oligodendroglioma) to be treated is characterized by the presence of an IDH1 mutation and an IDH2 mutation, wherein the IDH1 and IDH2 mutations collectively result in accumulation of R(-)-2-hydroxyglutarate (2HG) in a patient. In one aspect of these embodiments, the IDH1 and IDH2 mutations result in accumulation of R(-)-2-hydroxyglutarate (2HG) in a patient by providing a new ability of the enzyme to catalyze the NADPH dependent reduction of a ketoglutarate to R(-)-2-hydroxyglutarate (2HG) in a patient. In various aspects of these embodiments, the IDH1 mutation is an R132X mutation selected from R132H, R132C, R132L, R132V, R132S and R132G. In various aspects of these embodiments, the IDH2 mutation is an R140Q, R140W, R140L, R172K or R172G mutation. In various other aspects of these embodiments, the brain tumor (e.g., glioma (including low grade glioma), glioblastoma (including secondary glioblastoma), grade II or III astrocytoma, grade II or III oligodendroglioma) to be treated is characterized by any combination of the foregoing IDH1 and IDH2 mutations. In still other aspects of these embodiments, at least 30, 40, 50, 60, 70, 80 or 90% of the brain tumor (e.g., glioma (including low grade glioma), glioblastoma (including secondary glioblastoma), grade II or III astrocytoma, grade II or III oligodendroglioma) cells carry an IDH1 R132X mutation, such as an R132H, R132C, R132L, R132V, R132S or R132G mutation, and an IDH2 R140X and/or R172X mutation, such as an R140Q, R140W, or R140L and/or R172K or R172G mutation, at the time of diagnosis or treatment. A brain tumor (e.g., glioma (including low grade glioma), glioblastoma (including secondary glioblastoma), grade II or III astrocytoma, grade II or III oligodendroglioma) can be analyzed by sequencing cell samples to determine the presence and specific nature of (e.g., the changed amino acid present at) a mutation at amino acid 132 of IDH1 and at amino acid 140 and/or 172 of IDH2.

In still other embodiments, the brain tumor (e.g., glioma (including low grade glioma), glioblastoma (including secondary glioblastoma), grade II or III astrocytoma, grade II or III oligodendroglioma) to be treated is characterized by the presence of an IDH1 allele that does not include an R132X mutation and an IDH2 allele that does not include an R140X or R172X mutation. In one aspect of these embodiments, at least 90% of the brain tumor (e.g., glioma (including low grade glioma), glioblastoma (including secondary glioblastoma), grade II or III astrocytoma, grade II or III oligodendroglioma) cells do not include a mutation at amino acid 132 of IDH1 or at amino acid 140 or 172 of IDH2 at the time of diagnosis or treatment. A brain tumor (e.g., glioma (including low grade glioma), glioblastoma (including secondary glioblastoma), grade II or III astrocytoma, grade II or III oligodendroglioma) can be analyzed by sequencing cell samples to determine the presence or absence of a mutation at amino acid 132 of IDH1 and at amino acid 140 and/or 172 of IDH2.

Combination Therapies

In some embodiments, the methods described herein comprise the additional step of co-administering to a subject in need thereof an additional therapeutic modality (e.g., an additional cancer therapeutic agent, an additional therapeutic agent to minimize the symptoms of the cancer or the side effects of the cancer treatment or an additional cancer treatment). Exemplary additional cancer therapeutic agents (anti-cancer medications) include for example, chemotherapy with cytotoxic or cytostatic agents, targeted therapy (targeted medications), antibody therapies, immunotherapy, and hormonal therapy. Exemplary additional therapeutic agents (medications) to minimize symptoms and side effects include, for example, anti-epileptic medications, anti-seizure medications and anti-emesis medications. Additional cancer treatments include, for example, surgery, and radiation therapy. Examples of each of these treatments are provided below.

The term "co-administering" as used herein with respect to an additional cancer therapeutic agents means that the additional cancer therapeutic agent may be administered together with a compound of one aspect of this invention as part of a single dosage form (such as a composition of one aspect of this invention comprising a compound of one aspect of the invention and an second therapeutic agent as described above) or as separate, multiple dosage forms. Alternatively, the additional cancer therapeutic agent may be administered prior to, consecutively with, or following the administration of a compound of one aspect of this invention. In such combination therapy treatment, both the compounds of one aspect of this invention and the second therapeutic agent(s) are administered by conventional methods. The administration of a composition of one aspect of this invention, comprising both a compound of one aspect of the invention and a second therapeutic agent, to a subject does not preclude the separate administration of that same therapeutic agent, any other second therapeutic agent or any compound of one aspect of this invention to said subject at another time during a course of treatment. The term "co-administering" as used herein with respect to an additional cancer treatment means that the additional cancer treatment may occur prior to, consecutively with, concurrently with or following the administration of a compound of one aspect of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

Additional Therapeutic Modalities for Brain Cancers

Additional Therapeutic Modalities to be used in combination with the methods for treating brain cancers described herein include those therapeutic modalities (e.g., surgery, radiation, therapeutic agents/medications) that are known to be useful for treating brain tumors, i.e., having a therapeutic effect on, alleviating one or more symptoms of, altering the progression of, eradicating, reducing the size of, slowing or inhibiting the growth of, delaying or minimizing one or more symptoms associated with, reducing the malignancy of, or inducing stasis of the brain tumor, or alleviating or minimizing one or more side effects associated with another therapy applied or administered to treat the brain tumor.

In some embodiments, the additional therapeutic modality is surgery.

In some embodiments, the additional therapeutic modality is radiation therapy. In some embodiments, the radiation therapy is administered in a manner consistent with the National Comprehensive Cancer Network Clinical Practice Guidelines in Oncology (e.g., dose and schedule of administration), version 1.2016 available at nccn.org. In some embodiments, the radiation therapy is administered in a cumulative dose of 20-100 Gy, or 30-80 Gy, or 30-60 Gy, or 40-70 Gy, or 40-60 Gy, or 30-40 Gy, or 40-50 Gy, or 50-60 Gy, or 45-55 Gy, in 1.0-5.0 Gy fractions, or 1.5-3.0 Gy fractions, or 1.0-1.5 Gy fractions, or 1.5-2.0 Gy fractions, or 2.0-2.5 Gy fractions, or 2.5-3.0 Gy fractions, or 1.8-2.0 Gy fractions, or 1.8 Gy fractions, or 2.0 Gy fractions. In some embodiments, the radiation therapy is administered in a cumulative dose of 50-70 Gy in 1.5-2.5 Gy fractions, or 60 Gy in 2.0 Gy fractions. The cumulative dose refers to the total of all of the fractional doses given during a course of treatment.

The dose of radiation therapy may be selected based on the nature of the brain tumor. In some embodiments where the brain tumor is a low grade glioma, the radiation therapy is administered in a cumulative dose of 40-50 Gy in 1.5-2.5 Gy fractions, or in a cumulative dose of 45-54 Gy in 1.8-2.0 Gy fractions, or in a cumulative dose of 45.5 Gy in 1.8-2.0 Gy fractions. In some embodiments where the brain tumor is a high grade glioma, the radiation therapy is administered in a cumulative dose of 50-70 Gy in 1.5-2.5 Gy fractions, or in a cumulative dose of 59.4 Gy in 1.8 Gy fractions, or in a cumulative dose of 55.8-59.4 Gy in 1.8 Gy fractions, or in a cumulative dose of 57 Gy in 1.9 Gy fractions, or in a cumulative dose of 60 Gy in 1.8-2.0 Gy fractions, or 25 Gy in 5.0 Gy fractions. In some embodiments where the brain tumor is a glioblastoma, the radiation therapy is administered in a cumulative dose of 30-60 Gy in 2.0-4.0 Gy fractions, or in a cumulative dose of 34 Gy in 3.4 Gy fractions, or in a cumulative dose of 35-45 Gy in 2.5-3.0 Gy fractions, or in a cumulative dose of 50 Gy in 2.5 Gy fractions.

In some embodiments, the additional therapeutic modality is one or more additional therapeutic agents.

In some embodiments, the one or more additional therapeutic agents include one or more of an additional cancer therapy (i.e., anti-cancer medication) (e.g., DNA-reactive agent, a PARP inhibitor, an immunotherapy (e.g., a checkpoint inhibitor), PVC chemotherapy, an antibody therapy (e.g., bevacizumab), gemcitabine), an anti-emesis agent, an anti-convulsant or anti-epileptic agent.

In some embodiments, the one or more additional therapeutic agents is an additional cancer therapy (e.g., an anti-cancer medication).

In some embodiments, the additional cancer therapy is a DNA-reactive agent. As used herein, "DNA-reactive agents" are those agents, such as alkylating agents, cross-linking agents, and DNA intercalating agents, which interact covalently or non-covalently with cellular DNA. For example, DNA-reactive agents include adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, mitozolomide, nedaplatin, oxaliplatin, piposulfan, procarbazine, semustine, streptozocin, temozolomide, thiotepa, treosulfan, diethylnitrosoamine, benzo(a)pyrene, doxorubicin, mitomycin-C, and the like. Many of these DNA-reactive agents are useful in cancer therapy as DNA-reactive chemotherapeutic agents.

In some embodiments, the DNA-reactive agent is temozolomide (TMZ). In one aspect of these embodiments, the TMZ is administered in a manner consistent with the National Comprehensive Cancer Network Clinical Practice Guidelines in Oncology (e.g., dose and schedule of administration), version 1.2016 available at nccn.org. In one aspect of these embodiments, the TMZ is administered in a manner consistent with the prescribing information for TEMODAR® (temozolomide) Capsules and TEMODAR® (temozolomide) for Injection. In some aspects of these embodiments, the TMZ is administered in a daily dose of 100-250 mg/m2 based on the patient's body surface area, or 100-150 mg/m2, or 150-200 mg/m2, or 200-250 mg/m2. In some aspects of these embodiments, the TMZ is administered in a daily dose of 50-100 mg/m2 based on the patient's body surface area, or 50-75 mg/m2, or 75-100 mg/m2, or 60-90 mg/m2, or 65-85 mg/m2, or 70-80 mg/m2. In some aspects of these embodiments, the TMZ is administered in a daily dose of 125-175 mg/m2 based on the patient's body surface area for 5 consecutive days of a 28-day treatment cycle. In some aspects of these embodiments, the TMZ is administered in combination with radiation therapy in a daily dose of 50-100 mg/m2 based on the patient's body surface area, or 50-75 mg/m2, or 75-100 mg/m2, or 60-90 mg/m2, or 65-85 mg/m2, or 70-80 mg/m2. In some aspects of these embodiments, the TMZ is administered in combination with radiation therapy in a daily dose of 70-80 mg/m2 based on the patient's body surface area for 42 days. In some aspects of these embodiments where the brain tumor is a high grade glioma or glioblastoma, the TMZ is administered in combination with radiation therapy in a daily dose of 70-80 mg/m2 based on the patient's body surface area for 42 days. In some aspects of these embodiments where the brain tumor is an anaplastic astrocytoma, the TMZ is administered in a daily dose of 125-175 mg/m2 based on the patient's body surface area for 5 consecutive days of a 28-day treatment cycle. In some aspects of these embodiments where the brain tumor is an anaplastic astrocytoma, the TMZ is administered in a daily dose of 175-225 mg/m2 based on the patient's body surface area for 5 consecutive days of a 28-day treatment cycle.

In some embodiments, the one or more additional cancer therapies (anti-cancer medications) is a PARP inhibitor. As used herein, "PARP inhibitor" refers to an inhibitor of the enzyme poly ADP ribose polymerase (PARP). Examples of PARP inhibitors include pamiparib, olaparib, rucaparib, velaparib, iniparib, talazoparib, niraparib, and the like.

In some embodiments, the one or more additional cancer therapies (anti-cancer medications) is an immunotherapy, for example a checkpoint inhibitor. As used herein, "checkpoint inhibitor" refers to a therapeutic agent that inhibits an immune checkpoint (e.g., CTLA-4, PD-1/PD-L1, and the like) that otherwise would prevent immune system attacks on cancer cells, thereby allowing the immune system to attack the cancer cells. Examples of check point inhibitors include ipilimumab, nivolumab, pembrolizumab, atezolizumab, avelumab, durvalumab, BGB-A317, spartalizumab, and the like.

In some embodiments, the one or more additional cancer therapies (anti-cancer medications) is PVC chemotherapy. As used herein, "PVC chemotherapy" refers to a chemotherapy regimen comprising the combined administration of procarbazine, lomustine (which is sold under the trade name CCNU®), and vincristine (which is sold under the trade name Onocovin®). Typically, the vincristine is administered intravenously, while the procarbazine, and lomustine are administered orally. PCV chemotherapy often is administered in cycles, wherein each cycle comprises a single administration of vincristine and lomustine and a 10-day course of treatment with procarbazine.

In some embodiments, the one or more additional cancer therapies (anti-cancer medications) is an antibody, for example bevacizumab. Bevacizumab, which is sold under the trade name Avastin®, is a recombinant humanized monoclonal antibody.

In some embodiments, the one or more additional cancer therapies (anti-cancer medications) is gemcitabine. Gemcitabine, which is sold under the trade name Gemzar®, is a pyrimidine nucleoside analog.

In some embodiments, the one or more additional therapeutic agents is an anti-emesis agent. As used herein, "anti-emesis agent" refers to a drug that is effective to reduce vomiting and nausea symptoms. Examples of anti-emesis agents include 5-HT3 receptor antagonists (e.g., dolasetron, granisetron, ondansetron, tropisetron, palonosetron, mirtazapine, and the like), dopamine agonists (e.g., domperidone, olanzapine, droperidol, haloperidol, chlorpromazine, prochlorperazine, alizapride, prochlorperazine, metoclopramide, and the like), NK1 receptor antagonists (e.g., aprepitant, casopitant, rolapitant, and the like), antihistamines (e.g., cinnarizine, cyclizine, diphenhydramine, dimenhydrinate, doxylamine, meclizine, promethazine, hydroxyzine, and the like), cannabinoids (e.g, cannabis, dronabinol, synthetic cannabinoids, and the like), benzodiazepines (e.g., midazolam, lorazepam, and the like), anticholinergics (e.g., scopolamine and the like), steroids (e.g., dexamethasone and the like), trimethobenzamide, ginger, propofol, glucose/fructose/phosphoric acid (which is sold under the trade name Emetrol®), peppermint, muscimol, ajwain, and the like.

In some embodiments, the one or more additional therapeutic agents is an anti-convulsant or anti-epileptic agent. As used herein, "anti-convulsant or anti-epileptic agent" refers to a drug that is effective for treating or preventing seizures, including epileptic seizures. Examples of anti-convulsants include paraldehyde, stiripentol, phenobarbital, methylphenobarbital, barbexaclone, clobazam, clonazepam, clorazepate, diazepam, midazolam, lorazepam, nitrazepam, temazepam, nimetazepam, potassium bromide, felbamate, carbamazepine, oxcarbazepine, eslicarbazepine acetate, valproic acid, sodium valproate, divalproex sodium, vigabatrin, progabide, tiagabine, topiramate, gabapentin, pregabalin, ethotoin, phenytoin, mephenytoin, fosphenytoin, paramethadione, trimethadione, ethadione, beclamide, primidone, brivaracetam, etiracetam, levetiracetam, seletracetam, ethosuximide, phensuximide, mesuximide, acetazolamide, sultiame, methazolamide, zonisamide, lamotrigine, phenetunide, phenacemide, valpromide, valnoctamide, perampanel, stiripentol, pyridoxine, and the like.

EXAMPLES

General Experimental Notes:

In the following examples, the reagents (chemicals) were purchased from commercial sources (such as Alfa, Acros, Sigma Aldrich, TCI and Shanghai Chemical Reagent Company), and used without further purification. Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA) or Shimadzu LCMS-2020 Mass Spectrometer (Shimadzu, Japan). Microwave reactions were run on an Initiator 2.5 Microwave Synthesizer (Biotage, Sweden).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%. The chemical name of each of the exemplary compound described below is generated by ChemDraw software.

Abbreviations List

General
  anhy. anhydrous
  aq. aqueous
  min minute(s)
  hrs hours
  mL milliliter
  mmol millimole(s)
  mol mole(s)
  MS mass spectrometry
  NMR nuclear magnetic resonance
  TLC thin layer chromatography
  HPLC high-performance liquid chromatography
  satd. saturated
Spectrum
  Hz hertz
  δ chemical shift
  J coupling constant
  s singlet
  d doublet
  t triplet
  q quartet
  m multiplet
  br broad
  qd quartet of doublets
  dquin doublet of quintets
  dd doublet of doublets
  dt doublet of triplets
Solvents and Reagents
  DAST diethylaminosulfurtrifluoride
  $CHCl_3$ chloroform
  DCM dichloromethane
  DMF dimethylformamide
  $Et_2O$ diethyl ether
  EtOH ethyl alcohol
  EtOAc ethyl acetate
  MeOH methyl alcohol
  MeCN acetonitrile
  PE petroleum ether
  THF tetrahydrofuran
  DMSO dimethyl sulfoxide
  AcOH acetic acid
  HCl hydrochloric acid
  $H_2SO_4$ sulfuric acid
  $NH_4Cl$ ammonium chloride
  KOH potassium hydroxide
  NaOH sodium hydroxide
  $K_2CO_3$ potassium carbonate
  $Na_2CO_3$ sodium carbonate
  TFA trifluoroacetic acid
  $Na_2SO_4$ sodium sulfate
  $NaBH_4$ sodium borohydride
  $NaHCO_3$ sodium bicarbonate
  NaHMDS sodium hexamethyldisilylamide
  LiHMDS lithium hexamethyldisilylamide
  LAH lithium aluminum hydride
  $NaBH_4$ sodium borohydride
  LDA lithium diisopropylamide
  $Et_3N$ triethylamine
  Py pyridine
  DMAP 4-(dimethylamino)pyridine
  DIPEA N,N-diisopropylethylamine
  Xphos 2-dicyclohexylphosphino-2,4,6-triisopropylbiphenyl
  BINAP 2,2'-bis(diphenylphosphanyl)-1,1'-binaphthyl
  dppf 1,1'-bis(diphenylphosphino)ferrocene
  TBTU 2-(1H-benzotriazole-1-yl)-1,1,3,3-tetramethyluronium tetrafluoroborate
  DPPA diphenylphosphoryl azide
  $NH_4OH$ ammonium hydroxide
  EDCI 1-ethyl-3-(3-dimethylaminopropyl)carbodiimide
  HOBt 1-hydroxybenzotriazole
  Py Pyridine
  Dppf 1,1'-bis(diphenylphosphino)ferrocene
  HATU O-(7-azabenzotriazol-1-yl)-N,N,N',N'-tetramethyluronium BINAP 2,2'-bis(diphenylphosphanyl)-1,1'-binaphthyl
MTBE methyl tert-butyl ether
NaSMe sodium methoxide Example 1

Preparation of 6-(6-(methylthio)pyridin-2-yl)-N2,N4-bis((R)-1,1,1-trifluoropropan-2-yl)-1,3,5-triazine-2,4-diamine (Compound 1)

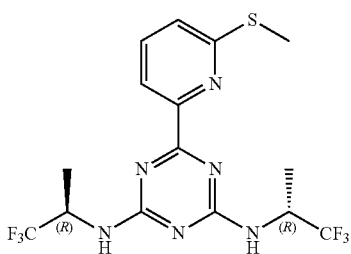

Compound 1

DMSO (500 mL) and 6-(6-chloropyridin-2-yl)-N2,N4-bis((R)-1,1,1-trifluoropropan-2-yl)-1,3,5-triazine-2,4-diamine (AG-881 free base, 100 g, 0.241 mol) were charged into a 1 L flask under N2 at 15-20° C. The resulting solution was stirred for 10 min at 15-20° C. to form a clear brown solution. The reaction solution was cooled to 5° C. and sodium thiomethoxide (NaSMe, 35.6 g, 0.508 mol) was added in portions over 20 min at 5-10° C. The reaction mixture was stirred at 20-25° C. for 3 h. The mixture was poured into ice water (3 L) at 5-10° C. with stirring. After 30 min at 20-25° C., the solid was filtered and the wet cake was triturated with water (1.5 L) over 30 min at 20-25° C. The solid was filtered, washed with water (200 mL) and dried in vacuum oven at 50-55° C. to afford 6-(6-(methylthio)pyridin-2-yl)-N2,N4-bis((R)-1,1,1-trifluoropropan-2-yl)-1,3,5-triazine-2,4-diamine as an off-white solid (100.8 g, 98% yield).

$^1$H NMR: (400 MHz, DMSO-$d_6$) δ 8.41-7.81 (m, 4H), 7.45-7.42 (m, 1H), 5.12-4.91 (m, 2H), 2.59 (s, 3H), 1.34 (d, J=6.1 Hz, 6H). $^{13}$C-NMR: (101 MHz, DMSO-$d_6$) δ 170.65, 170.24, 166.65, 166.38, 160.58, 160.15, 154.20 (d, J=14.4 Hz), 137.77, 127.99, 125.19, 122.87, 122.34, 119.89, 119.76 (d, J=21.9 Hz), 47.44, 47.13, 13.89 (d, J=9.6 Hz), 13.53, 13.23.

LC-MS (ESI): m/z 427 [M+H]$^+$

Example 2

Preparation of 6-(6-(methylsulfinyl)pyridin-2-yl)-N2,N4-bis((R)-1,1,1-trifluoropropan-2-yl)-1,3,5-triazine-2,4-diamine (Compound 2)

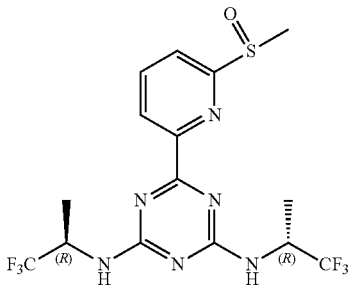

Compound 2

MeOH (48 mL) and 6-(6-(methylthio)pyridin-2-yl)-N2,N4-bis((R)-1,1,1-trifluoropropan-2-yl)-1,3,5-triazine-2,4-diamine (4.0 g, 9.38 mmol) were charged into a 250 mL flask at 10-20° C. The reaction mixture was stirred for 10 min to get a clear solution. To the reaction solution was added aqueous Oxone solution (4.6 g, 7.48 mmol, 40 mL water) dropwise over 30 min at 5-15° C. The resulting mixture was stirred for 2 h at 20-30° C. The mixture was then cooled to 10° C. and quenched with water (100 mL). The reaction mixture was then extracted with DCM (1×100 mL). The aqueous phase was extracted with DCM (20 mL). The combined organic phase was cooled to 5-10° C. and added aqueous solution of Na$_2$SO$_3$ (1.18 g, 9.38 mmol, 20 mL water) [The addition is exothermic]. The phases were separated, and the organic phase was washed with water (1×40 mL), dried over anhydrous Na$_2$SO$_4$, filtered and concentrated in vacuum at 40-45° C. to get the crude product as an oil. The residue was purified by silica gel chromatography (Elutant: n-heptane/EtOAc—5:1 to 1:1). The combined pure fractions were concentrated and dried under vacuum to afford the intended product as a white solid. The product was further recrystallized by dissolving it in methanol (30 mL) at 40-45° C., followed by the addition of water (60 mL) over a period of 30 min at 20-30° C. The resulting suspension was stirred for an additional 0.5 h at 20-30° C. before being filtered, washed with water (10 mL) and dried in a vacuum oven at 50-55° C. to afford 6-(6-(methylsulfinyl)pyridin-2-yl)-N2,N4-bis((R)-1,1,1-trifluoropropan-2-yl)-1,3,5-triazine-2,4-diamine as a white solid (2.2 g, 53% yield).

$^1$H-NMR (400 MHz, DMSO-$d_6$) δ 8.57-8.41 (m, 2H), 8.35-8.22 (m, 2H), 8.05 (dd, J=26.2, 7.4 Hz, 1H), 5.13-4.88 (m, 2H), 2.82 (s, 3H), 1.34 (d, J=6.8 Hz, 6H).

$^{13}$C-NMR (101 MHz, DMSO-$d_6$) δ 169.86, 169.51, 166.67, 166.37, 166.32, 166.11, 154.56 (d, J=9.7 Hz), 140.05 (d, J=8.1 Hz), 130.61, 127.93, 126.80, 125.33, 125.22, 124.98, 124.64, 121.02 (d, J=16.8 Hz), 47.49, 47.12 (d, J=13.5 Hz), 41.60 (d, J=13.5 Hz), 13.87 (d, J=15.2 Hz).

LC-MS (ESI): m/z 443 [M+H]+.

Example 3

Preparation of 6-(4, 6-bis(((R)-1,1,1-trifluoropropan-2-yl)amino)-1,3,5-triazin-2-yl)pyridine-2-thiol (Compound 3)

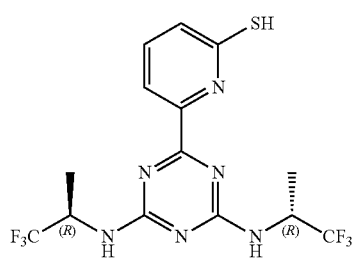

Compound 3

DMSO (100 mL) and 6-(6-chloropyridin-2-yl)-N2,N4-bis((R)-1,1,1-trifluoropropan-2-yl)-1,3,5-triazine-2,4-diamine (AG-881 free base, 10 g, 24.1 mmol) were charged into a 250 mL flask under N2 at 15-20° C. The resulting solution was stirred for 10 min at 15-20° C. to get a clear brown solution. The reaction mixture was cooled to 5° C., and was added Na$_2$S (4.2 g, 90% purity, 24.4 mmol) in portions over 5 min at 5-10° C. The reaction mixture was stirred for 16 h at 20~25° C., poured into ice water (500 mL) and acetic acid (50 mL) was added at 5~10° C. with stirring. After stirring for 15-30 min at 10-15° C., the solid was filtered. The wet cake was dissolved in DCM (100 mL), phase separated, and the aqueous layer was discarded. The organic phase was dried with anhydrous Na$_2$SO$_4$, filtered and concentrated under reduced pressure to obtain the crude product as light yellow oil. The crude product was purified by silica gel chromatography (Elutant: DCM/MeOH—30:1 to 10:1). The pure fractions containing product were combined and concentrated under reduced pressure to afford the purified product as yellow solid which was further dried in vacuum oven at ambient temperature to obtain 6-(4, 6-bis(((R)-1,1,1-trifluoropropan-2-yl)amino)-1,3,5-triazin-2-yl)pyridine-2-thiol as a yellow solid (8.0 g, 80% yield).

$^1$H-NMR (400 MHz, DMSO-d$_6$) δ 12.68-11.90 (m, 1H), 8.68-7.66 (m, 2H), 7.61-7.48 (m, 3H), 5.36-4.86 (m, 2H), 1.37-1.34 (m, 6H).

$^{13}$C-NMR (101 MHz, DMSO-d$_6$) δ 179.09, 178.77, 166.12, 165.71, 165.62, 163.46, 142.85, 142.66, 137.97, 137.62, 136.76, 136.35, 127.83, 125.02, 113.60, 112.82, 47.60-47.17, 14.0 (d, J=16.2 Hz).

LC-MS (ESI): m/z 413 [M+H]$^+$.

Example 4

Preparation of 6,6'-(6,6'-disulfanediylbis(pyridine-6,2-diyl))bis(N2,N4-bis((R)-1,1,1-trifluoropropan-2-yl)-1,3,5-triazine-2,4-diamine) (Compound 4)

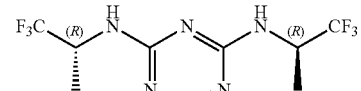

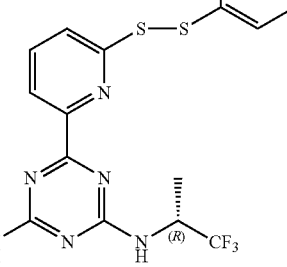

Acetonitrile (30 mL) and 6-(4, 6-bis(((R)-1,1,1-trifluoropropan-2-yl)amino)-1,3,5-triazin-2-yl)pyridine-2-thiol (1.0 g, 2.43 mmol) were charged into a 100 mL flask under N2 at 15-20° C. The reaction mixture was cooled to −20° C., and trichloroisocyanuric acid (102 mg, 0.44 mmol) was added in one portion. The resulting mixture was stirred for 1 h at −20° C. and the solid was filtered. The filtrate was poured into water (50 mL), and the resulting solution was extracted with ethyl acetate (1×50 mL). The organic layer was concentrated under reduced pressure to afford the crude product as light yellow oil. The residue was purified by silica gel chromatography (Elutant: DCM/MeOH—50:1 to 20:1). The pure fractions containing product were combined and concentrated to afford a pale yellow solid which was further dried in vacuum oven at ambient temperature to obtain 6,6'-(6,6'-disulfanediylbis(pyridine-6,2-diyl))bis(N2,N4-bis((R)-1,1,1-trifluoropropan-2-yl)-1,3,5-triazine-2,4-diamine) as a pale yellow solid (0.82 g, 82% yield).

$^1$H-NMR (400 MHz, DMSO-d$_6$) δ 8.62 (d, J=8.0 Hz, 1H), 8.54 (d, J=8.0 Hz, 2H), 8.27-8.24 (m, 2H), 8.19 (d, J=8.0 Hz, 2H), 8.07-8.02 (m, 2H), 7.87 (d, J=8.0 Hz, 2H), 5.14-4.92 (m, 4H), 1.41-1.36 (m, 12H).

$^{13}$C-NMR (101 MHz, DMSO-d$_6$) δ 169.85, 169.59, 166.70, 166.42, 166.33, 158.67, 158.53, 158.28, 154.71, 139.72 (d, J=12.1 Hz), 130.77, 127.96, 125.15, 122.21, 121.79, 121.46, 121.32, 121.14, 121.04, 47.78-46.88, 13.94 (d, J=11.1 Hz).

LC-MS (ESI): m/z 823 [M+H]$^+$.

Example 5

Preparation of (R)-2-amino-3-((6-(4,6-bis(((R)-1,1,1-trifluoropropan-2-yl)amino)-1,3,5-triazin-2-yl-pyridin-2-yl)thio)propanoic acid (Compound 5)

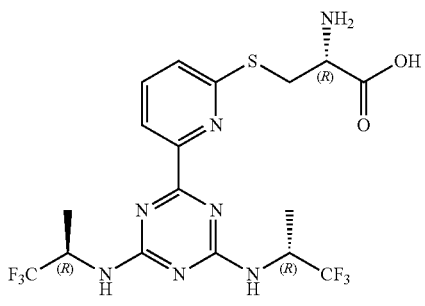

Compound 5

N,N-Dimethylformamide (5 mL), N,N-Diisopropylethylamine (1.88 g, 14.6 mmol) and 6-(4, 6-bis(((R)-1,1,1-trifluoropropan-2-yl)amino)-1,3,5-triazin-2-yl)pyridine-2-thiol (1.0 g, 2.43 mmol) were charged into a 25 mL flask under N2 at 20-30° C. A solution of L-2-amino-3-chloropropanoic acid (0.60 g, 4.86 mmol) in water (5 mL) was then added dropwise to the reaction mixture at 20-30° C. The resulting mixture was heated to 60° C. and stirred for 20 h. After stirring for 20 h at 60° C. the mixture was cooled to 20° C. and poured into water (30 mL). The resulting slurry was stirred for 15-30 min and then the solid was isolated by vacuum filtration and washed with water (10 mL). The solid was dried on filter under air for 1-2 h and then was dissolved in DMSO (30 mL). The product solution in DMSO was then purified by preparative HPLC [column: YMC TA C18, 250×21.2 mm, 10 um; flow: 15 mL/min.; Gradient: 20% Acetonitrile-80% water 0.1% TFA to 70% Acetonitrile-30% water 0.1% TFA; @254/205 nm]. The pure fractions containing product were combined and concentrated in vacuum at 45-50° C. to remove solvents. The product was then lyophilized to afford (R)-2-amino-3-((6-(4,6-bis(((R)-1,1,1-trifluoropropan-2-yl)amino)-1,3,5-triazine-2-yl)pyridin-2-yl)thio)propanoic acid as a white solid (170 mg, 98.9%/220 nm, 14% yield).

$^1$H-NMR (400 MHz, DMSO-$d_6$) δ 8.37-8.03 (m, 6H), 7.88 (t, J=8.0 Hz, 1H), 7.63 (d, J=8.0 Hz, 1H), 5.19-4.95 (m, 2H), 3.61-3.32 (m, 3H), 1.42-1.35 (m, 6H).

$^{13}$C-NMR (101 MHz, DMSO-$d_6$) δ 169.53, 169.27, 168.77, 166.31, 166.21, 166.14, 159.03 (d, J=8.1 Hz), 153.24 (d, J=4.0 Hz), 138.70 (d, J=7.1 Hz), 127.96, 125.35 (d, J=17.2 Hz), 120.71, 120.20, 56.44, 47.61, 33.77, 13.97.

LC-MS (ESI): m/z 499 [M+H]$^+$

Example 6

Preparation of (S)-3-((6-(4,6-bis(((R)-1,1,1-trifluoropropan-2-yl)amino)-1,3,5-triazin-2-yl)pyridin-2-yl)thio)-2-methylpropanoic acid (Compound 6)

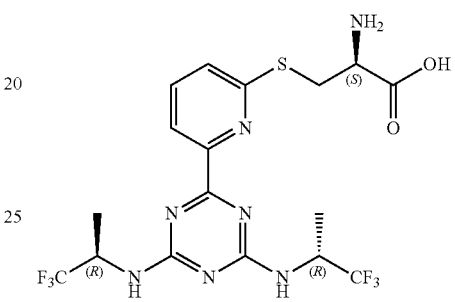

Compound 6

N,N-Dimethylformamide (5 mL), N,N-Diisopropylethylamine (3.1 g, 24.3 mmol) and 6-(4, 6-bis(((R)-1,1,1-trifluoropropan-2-yl)amino)-1,3,5-triazin-2-yl)pyridine-2-thiol (1.0 g, 2.43 mmol) were charged into a 25 mL flask under N2 at 20-30° C. A solution of L-2-amino-3-chloropropanoic acid (0.60 g, 4.86 mmol) in water (5 mL) was then added dropwise to the reaction mixture at 20-30° C. The resulting mixture was heated to 60° C. and stirred for 20 h. After stirring for 20 h at 60° C. the mixture was cooled to 20° C. and poured into water (30 mL). The resulting slurry was stirred for 15-30 min and then the solid was isolated by vacuum filtration and washed with water (10 mL). The solid was dried on filter under air for 1-2 h and then was dissolved in DMSO (30 mL). The product solution in DMSO was then purified by preparative HPLC [column: YMC TA C18, 250×21.2 mm, 10 um; flow: 15 mL/min.; Gradient: 20% Acetonitrile-80% water 0.1% TFA to 70% Acetonitrile-30% water 0.1% TFA; @254/205 nm]. The pure fractions containing product were combined and concentrated in vacuum at 45-50° C. to remove solvents. The product was then lyophilized to afford (S)-3-((6-(4,6-bis(((R)-1,1,1-trifluoropropan-2-yl)amino)-1,3,5-triazin-2-yl)pyridine-2-yl)thio)-2-methylpropanoic acid as a white solid (120 mg, 98.5%/220 nm, 10% yield).

$^1$H-NMR (400 MHz, DMSO-$d_6$) δ 8.36-8.04 (m, 6H), 7.88 (t, J=8.0 Hz, 1H), 7.63 (d, J=8.0 Hz, 1H), 5.17-4.94 (m, 2H), 3.62-3.33 (m, 3H), 1.42-1.34 (m, 6H).

$^{13}$C-NMR (101 MHz, DMSO-$d_6$) δ 169.55, 169.28, 168.50, 166.29, 166.15, 159.07, 158.99, 153.22, 138.71 (d, J=7.1 Hz), 125.54, 125.38, 120.68, 120.17, 56.52, 47.59, 33.83, 13.99. LC-MS (ESI): m/z 499 [M+H]$^+$.

Example 7

Preparation of 6-(6-(methylsulfonyl)pyridin-2-yl)-N2,N4-bis((R)-1,1,1-trifluoropropan-2-yl)-1,3,5-triazine-2,4-diamine (Compound 7)

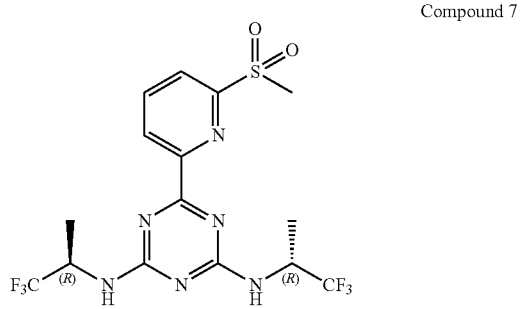

Compound 7

DMSO (50 mL) and 6-(6-chloropyridin-2-yl)-N2, N4-bis ((R)-1,1,1-trifluoropropan-2-yl)-1,3,5-triazine-2,4-diamine (AG-881 free base, 5.0 g, 12.06 mmole) were charged to a flask. The resulting mixture was stirred for 5 min at 15-20° C. to form a clear brown solution under nitrogen. The reaction mixture was cooled to 5° C., then added sodium thiomethoxide (NaSMe, 4.3 g, 60.28 mmole) was added in portions over 20 min at 5-10° C. under nitrogen. The reaction mixture was heated to 90-95° C., stirred for 3 h at 90-95° C. The reaction solution was poured into ice water (200 mL) at 5-10° C. with stirring. After stirring for 30 min, the solids were filtered, washed the filter cake with water (50 mL) and dried in vacuum at 50° C. for 6 h to afford 6-(6-(methylthio)pyridin-2-yl)-N2,N4-bis((R)-1,1,1-trifluoropropan-2-yl)-1,3,5-triazine-2,4-diamine as a pale yellow solid (4.8 g, 98.9% purity, 93% crude yield).

To a solution of MeOH (40 mL) and water (40 mL) was added 6-(6-(methylthio)pyridin-2-yl)-N2,N4-bis((R)-1,1,1-trifluoropropan-2-yl)-1,3,5-triazine-2,4-diamine (4.0 g, 9.38 mmol) in one portion. The reaction mixture was added with Oxone (11.5 g, 18.8 mmol) in portions over 15 min while keeping the temperature below 20° C. The reaction mixture was stirred for 2 h at 20-30° C. The reaction mixture was cooled to 10° C., then added water (80 mL) and DCM (120 mL). The resulting mixture was stirred for 10 min at 10-15° C. and separated. The organic phase was washed with aqueous $Na_2SO_3$ (1.2 g in 80 mL water) solution at 5-10° C. (check by KI starch paper) and separated. The organic phase was washed with water (100 mL×2) and separated. The organic phase was dried over anhydrous sodium sulfate, filtered and concentrated in vacuum at 40-45° C. to get 4-5V of slurry. The slurry was stirred for 30 min at 10-15° C., filtered, washed with MTBE (20 mL) and dried in vacuum at 50° C. to afford 6-(6-(methylsulfonyl)pyridin-2-yl)-N2, N4-bis((R)-1,1,1-trifluoropropan-2-yl)-1,3,5-triazine-2,4-diamine as a pale yellow solid (2.2 g, 98.7% purity, 51% yield). The mother liquor was concentrated to afford 6-(6-(methylsulfonyl)pyridin-2-yl)-N2,N4-bis((R)-1,1,1-trifluoropropan-2-yl)-1,3,5-triazine-2,4-diamine as a yellow solid (~1.5 g, ~90 a %/220 nm).

$^1$H-NMR (400 MHz, $CDCl_3$) δ 8.57 (t, J=8.0 Hz, 1H), 8.21 (d, J=8.0 Hz, 1H), 8.11 (t, J=8 Hz, 1H), 5.68 (d, J=12 Hz, 1H), 5.31 (d, J=8 Hz, 1H), 5.11 (b s, 1H), 4.88 (m, 1H), 3.34 (s, 3H), 1.43 (dd, J=8.0, 4.0 Hz, 6H).

$^{13}$C-NMR (100 MHz, $CDCl_3$) δ 169.24, 166.18, 158.23, 154.38, 139.17, 127.46, 125.45 (q), 122.69, 47.71, 40.01, 14.34.

LC-MS (ESI): m/z 459 [M+H]$^+$.

Example 8

Characterization of Absorption, Distribution, Metabolism, and Excretion of Oral [$^{14}$C]Vorasidenib with Concomitant Intravenous Microdose Administration of [$^{13}C_3$$^{15}N_3$] Vorasidenib in Humans Metabolite profiling and identification of vorasidenib (AG-881) was performed in plasma, urine, and fecal samples collected from five healthy subjects after a single 50-mg (100 μCi) oral dose of [14C]AG-881 and concomitant intravenous microdose of [$^{13}$C3 $^{15}$N3]AG-881.

Plasma samples collected at selected time points from 0 through 336 hour postdose were pooled across subjects to generate 0- to 72 and 96-336-hour area under the concentration-time curve (AUC)-representative samples. Urine and feces samples were pooled by subject to generate individual urine and fecal pools. Plasma, urine, and feces samples were extracted, as appropriate, the extracts were profiled using high performance liquid chromatography (HPLC), and metabolites were identified by liquid chromatography-mass spectrometry (LC-MS and/or LC-MS/MS) analysis and by comparison of retention time with reference standards, when available.

Due to low radioactivity in samples, plasma metabolite profiling was performed by using accelerator mass spectrometry (AMS). In plasma, AG-881 was accounted for 66.24 and 29.47% of the total radioactivity in the pooled $AUC_{0-72}$ h and $AUC_{9-336}$ plasma, respectively. The most abundant radioactive peak (P7; M458) represented 0.10 and 43.92% of total radioactivity for pooled $AUC_{0-72}$ and $AUC_{96-336\ h}$ plasma, respectively. All other radioactive peaks accounted for less than 6% of the total plasma radioactivity and were not identified.

The majority of the radioactivity recovered in feces was associated with unchanged AG-881 (55.5% of the dose), while no AG-881 was detected in urine. In comparison, metabolites in excreta accounted for approximately 18% of dose in feces and for approximately 4% of dose in urine. M515, M460-1, M499, M516/M460-2, and M472/M476 were the most abundant metabolites in feces, and each accounted for approximately 2 to 5% of the radioactive dose, while M266 was the most abundant metabolite identified in urine and accounted for a mean of 2.54% of the dose. The remaining radioactive components in urine and feces each accounted for <1% of the dose.

Overall, the data presented indicate [$^{14}$C]AG-881 underwent moderate metabolism after a single oral dose of 50-mg (100 μCi) and was eliminated in humans via a combination of metabolism and excretion of unchanged parent. AG-881 metabolism involved the oxidation and conjugation with glutathione (GSH) by displacement of the chlorine at the chloropyridine moiety. Subsequent biotransformation of GSH intermediates resulted in elimination of both glutamic acid and glycine to form the cysteinyl conjugates (M515 and M499). The cysteinyl conjugates were further converted by a series of biotransformation reactions such as oxidation, S-dealkylation, S-methylation, S-oxidation, S-acetylation and N-dealkylation resulting in the formation multiple metabolites.

A summary of the metabolites observed is included in Table 2

TABLE 2

| Component designation | Retention Time (Minutes) | [M + H]⁺ | Type of Biotransformation | Matrix Plasma | Urine | Feces |
|---|---|---|---|---|---|---|
| Unidentified 1 | 7.00 | | Unknown | | X | |
| M266 | 7.67[a] | 267 | N-dealkylation | | X | |
| Unidentified 2 | | | Unknown | | X | |
| Unidentified 3 | | | Unknown | | X | |
| Unidentified 4 | | | Unknown | | X | |
| Unidentified 5 | | | Unknown | | X | |
| M515 | 19.79[b] | 516 | Oxidation | | | X |
| M460-1 | 20.76[b] | 461 | Oxidation | | | X |
| M499 | 21.22[b] | 500 | Dechloro-glutathione conjugation + hydrolysis | | X | X |
| M516 | 21.89[b] | 517 | Oxidative-deamination | | | X |
| M460-2 | 21.98[b] | 461 | Oxidation | | | X |
| M472 | 22.76[b] | 473 | S-dealkylation + S-acetylation + reduction | | | X |
| M476 | 22.76[b] | 477 | Oxidation | | | X |
| Unidentified 6 | | | Unknown | | X | |
| M474 | 23.63[b] | 475 | Oxidation | | | X |
| Unidentified 7 | | | Unknown | | | X |
| M430 | 25.88[b] | 431 | AG-881-oxidation | | | X |
| M426 | 30.62[b] | 427 | S-dealkylation + methylation | | | X |
| M458 | 31.03[c] | 459 | AG-69460 | X | | * |
| AG-881 | 39.41[b] | 415 | AG-881 | X | | X |
| M428 | 47.40[b] | 429 | S-dealkylation + oxidation | | | X |

Table 3 contains a summary of protonated molecular ions and characteristic product ions for AG-881 and identified metabolites

TABLE 3

| Metabolite designation | Retention Time (Minutes) | [M + H]⁺ | Proposed Metabolite Identification | Characteristic Product Ions (m/z) | Matrix |
|---|---|---|---|---|---|
| M266 | 7.88[a] | 267 | (structure) | 188, 187 | Urine |
| M515 | 19.79[b] | 516 | (structure) | 429, 260, 164, 153 | Feces |

TABLE 3-continued
| Metabolite designation | Retention Time (Minutes) | [M + H]+ | Proposed Metabolite Identification | Characteristic Product Ions (m/z) | Matrix |
|---|---|---|---|---|---|
| M460-1 | 20.76[b] | 461 | 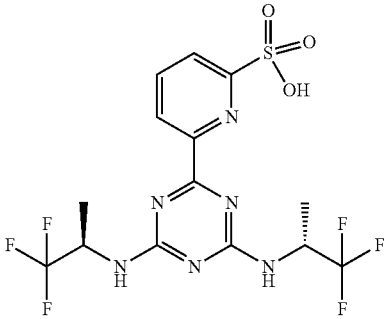 [SMILES: C[C@@H](Nc1nc(N[C@H](C)C(F)(F)F)nc(-c2cccc(S(=O)(=O)O)n2)n1)C(F)(F)F] | 379, 260, 164 | Feces |
| M499 | 21.22[b] | 500 | 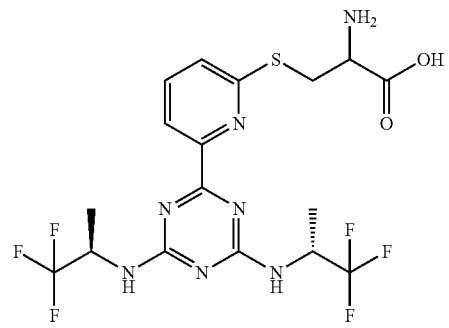 [SMILES: C[C@@H](Nc1nc(N[C@H](C)C(F)(F)F)nc(-c2cccc(SCC(N)C(=O)O)n2)n1)C(F)(F)F] | 437, 413, 260, 164, 137 | Urine Feces |
| M516 | 21.89[b] | 517 | 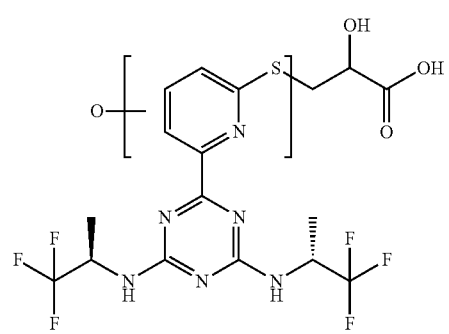 | 427, 260, 164, 153 | Feces |
| M460-2 | 21.98[b] | 461 | 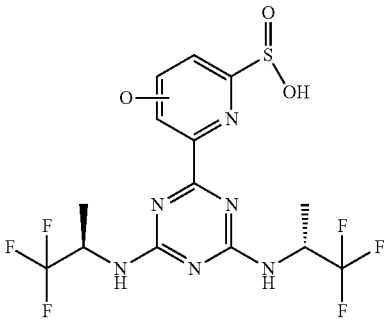 | 369, 260, 164, 139, 121, 93 | Feces |

TABLE 3-continued
| Metabolite designation | Retention Time (Minutes) | [M + H]+ | Proposed Metabolite Identification | Characteristic Product Ions (m/z) | Matrix |
|---|---|---|---|---|---|
| M472 | 22.76[b] | 473 | 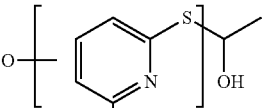 | 429, 260, 179, 164, 153 | Feces |
| M476 | 22.76[b] | 477 | | 395, 260, 164, 139, 119 | Feces |
| M474 | 23.63[b] | 475 | 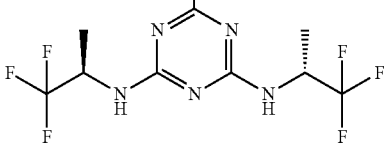 | 260, 164, 68 | Feces |
| M430 | 25.88[b] | 431 | 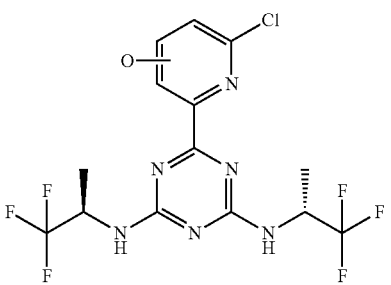 | 260, 164, 155, 68 | Feces |
| M426 | 30.62[b] | 427 | 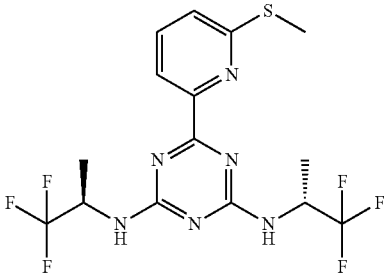 [SMILES: CSc1cccc(-c2nc(N[C@H](C)C(F)(F)F)nc(N[C@H](C)C(F)(F)F)n2)n1] | 260, 164, 151 | Feces |

TABLE 3-continued

| Metabolite designation | Retention Time (Minutes) | [M + H]+ | Proposed Metabolite Identification | Characteristic Product Ions (m/z) | Matrix |
|---|---|---|---|---|---|
| M458 | 31.03[b] | 459 | (structure: 6-(methylsulfonyl)pyridin-2-yl triazine with two (1,1,1-trifluoropropan-2-yl)amino substituents) | 380, 311, 260, 183, 164, 130 | Plasma Feces[d] |
| AG-881 | 39.41[b] | 415 | (structure: 6-chloropyridin-2-yl triazine with two (1,1,1-trifluoropropan-2-yl)amino substituents) | 319, 277, 260, 240, 164, 139, 119, 68 | Plasma Feces[d] |
| M428 | 47.40[b] | 429 | (structure: 6-(sulfenyl-OH)pyridin-2-yl triazine with two (1,1,1-trifluoropropan-2-yl)amino substituents) | 260, 164, 153 | Feces |

Notes
[a]Retention time from analysis of a urine sample
[b]Retention time from analysis of a feces sample
[c]Retention time from analysis of a plasma sample
[d]M458 was only detected in feces by mass spectrometry, not by radioprofiling.

The proposed (theoretical) biotransformation pathways leading to the observed metabolites are shown in FIG. 1.

Example 9

Enzymatic Assays
In Vitro Assays for IDH1m (R132H or R132C) Inhibitors

The following describes the experimental procedures that can be used to obtain the data in columns 2 and 4 of Table 4 and column 2 of Table 5.

In the primary reaction, the reduction of α-KG acid to 2HG is accompanied by a concomitant oxidation of NADPH to NADP. The amount of NADPH remaining at the end of the reaction time is measured in a secondary diaphorase/resorufin reaction in which the NADPH is consumed in a 1:1 molar ratio with the conversion of resazurin to the highly fluorescent resorufin. Uninhibited reactions exhibit a low fluorescence at the end of the assay, while reactions in which the consumption of NADPH by R132H IDH1 has been inhibited by a small molecule show a high fluorescence.

The primary reaction is performed in a volume of 50 μL 1× Buffer (150 mM NaCl, 20 mM Tris 7.5, 10 mM MgCl$_2$, 0.05% (w/v) bovine serum albumin), contained 0.25 ug/mL (2.7 nM) IDH1 wt/IDH1 R132H heterodimer, 0.3 mM alpha-ketoglutarate, 4 μM NADPH, and either 300 μM NADP (saturated) or 30 μM NADP (without saturation), and 1 uL of 50× compound in DMSO. The mixture of compound, enzyme, and cofactor is pre-incubated at room temperature for 1 hr prior to the addition of alpha-ketoglutarate. To perform the secondary reaction, 10 uL of 1× buffer containing 36 μg/ml diaphorase and 30 mM resazurin is added to the primary reaction and incubated for a further 5 minutes at 25° C. Florescence is read on a Spectramax platereader at Ex 544 Em 590. Compounds or compound dilutions are prepared in 100% DMSO concentration and diluted 1:50 into the final reaction. IDH1 wt/IDH1 R132C is assayed under similar conditions except that 1× Buffer is 50 mM K$_2$HPO$_4$, pH 6.5; 10 mM MgCl$_2$; 10% glycerol; 0.03% (w/v) bovine serum albumin and final concentrations are 0.4 ug/mL (4.3 nM) IDH1 wt/IDH1 R132C heterodimer, 0.02 mM alpha-ketoglutarate, 4 uM NADPH, and either 300 μM NADP (saturated) or 30 μM NADP (without saturation). IC50s are determined.

IDH1 or IDH2 wildtype (wt) and mutant heterodimers are expressed and purified by methods known in the art. For example, IDH1 wt/R132m heterodimer is expressed and purified as follows. Co-expression of IDH1 wt-his and IDH1R132C-flag is carried out in sf9 insect cells. Cells (25 g) are resuspended in 250 ml of 50 mM Tirs, 500 mM NaCl, pH7.4, at 4° C. with stirring. Cells are disrupted with 4 passes through an M-Y110 Micro fluidizer (Microfluidics) set to 500 psi, and then centrifuged at 22,000 rcf for 20 min at 4° C. The supernatant is harvested and loaded at 15 cm/h on a Histrap FF 5*1 ml column (GE) which is equilibrated with 50 mM Tirs, 500 mM NaCl, pH7.4. Host cell contaminants are removed by washing the column with equilibration buffer followed by equilibration buffer containing 20 mM imidazole and 60 mM imidazole to baseline. IDH1 wt-his homodimer and IDH1 wt-his/IDH1R132C-flag are eluted by equilibration buffer containing 250 mM imidazole. Fractions eluted by 250 mM imidazole are pooled together and loaded at 15 cm/h onto a column pre-packed with 10 ml ANTI-FLAG® M2 Affinity Gel (Sigma), the column is equilibrated with 50 mM Tris, 500 mM NaCl, pH7.4. After washing with equilibration buffer, IDH1 wt-his/IDH1R132C-flag heterodimer is eluted by equilibration buffer containing flag peptide (0.2 mg/ml). Aliquots of IDH1 wt-his/IDH1R132C-flag are flash frozen in liquid N2 and stored at −80° C. Same conditions are used for the purification of IDH1 wt-his/IDH1R132H-flag.

In Vitro Assays for IDH1m (R132H or R132C) Inhibitors

The following describes the experimental procedures that can be used to obtain the data in columns 3 and 6 of Table 4.

A test compound is prepared as 10 mM stock in DMSO and diluted to 50× final concentration in DMSO, for a 50 µl reaction mixture. IDH enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1-R132 homodimer enzyme is diluted to 0.125 µg/ml in 40 µl of Assay Buffer (150 mM NaCl, 20 mM Tris-Cl pH 7.5, 10 mM $MgCl_2$, 0.05% BSA, 2 mM b-mercaptoethanol); 1 µl of test compound dilution in DMSO is added and the mixture is incubated for 60 minutes at room temperature. The reaction is started with the addition of 10 µl of Substrate Mix (20 µl NADPH, 5 mM alpha-ketoglutarate, in Assay Buffer) and the mixture is incubated for 90 minutes at room temperature. The reaction is terminated with the addition of 25 µl of Detection Buffer (36 µg/ml diaphorase, 30 mM resazurin, in 1× Assay Buffer), and is incubated for 1 minute before reading on a SpectraMax platereader at Ex544/Em590.

Compounds are assayed for their activity against IDH1 R132C following the same assay as above with the following modifications: Assay Buffer is (50 mM potassium phosphate, pH 6.5; 40 mM sodium carbonate, 5 mM $MgCl_2$, 10% glycerol, 2 mM b-mercaptoethanol, and 0.03% BSA). The concentration of NADPH and alpha-ketoglutarate in the Substrate Buffer is 20 µM and 1 mM, respectively.

In Vitro Assays for IDH1m (R132H or R132C) Inhibitors

The following describes the experimental procedures that can be used to obtain the data in columns 3 and 5 of Table 5.

A test compound is prepared as 10 mM stock in DMSO and diluted to 50× final concentration in DMSO, for a 50 µl reaction mixture. IDH enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1-R132H homodimer enzyme is diluted to 0.125 µg/ml in 40 µl of Assay Buffer (150 mM NaCl, 20 mM Tris-Cl pH 7.5, 10 mM $MgCl_2$, 0.05% BSA, 2 mM b-mercaptoethanol) containing 5 µM NADPH and 37.5 µM NADP; 1 µl of test compound dilution in DMSO is added and the mixture is incubated for 60 minutes at room temperature. The reaction is started with the addition of 10 µl of Substrate Mix (20 µl NADPH, 5 mM alpha-ketoglutarate, in Assay Buffer) and the mixture is incubated for 60 minutes at room temperature. The reaction is terminated with the addition of 25 µl of Detection Buffer (36 µg/ml diaphorase, 30 mM resazurin, in 1× Assay Buffer), and is incubated for 1 minute before reading on a SpectraMax platereader at Ex544/Em590.

Compounds are assayed for their activity against IDH1 R132C following the same assay as above with the following modifications: IDH1-R132C homodimer enzyme is diluted to 0.1875 µg/ml in 40 µl of Assay Buffer (50 mM potassium phosphate, pH 6.5; 40 mM sodium carbonate, 5 mM $MgCl_2$, 10% glycerol, 2 mM b-mercaptoethanol, and 0.03% BSA) containing 5 uM NADPH and 28.75 uM NADP. The concentration of alpha-ketoglutarate in the Substrate Buffer is 1 mM.

In Vitro Assays for IDH2m R140Q Inhibitors

The following describes the experimental procedures used to obtain the data in column 7 of Table 4.

Compounds are assayed for IDH2 R140Q inhibitory activity through a cofactor depletion assay. Compounds are preincubated with enzyme, then the reaction is started by the addition of NADPH and α-KG, and allowed to proceed for 60 minutes under conditions previously demonstrated to be linear with respect for time for consumption of both cofactor and substrate. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 µl of 100× compound dilution series is placed, followed by the addition of 40 µl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 0.25 µg/ml IDH2 R140Q protein. The test compound is then incubated for one hour at room temperature with the enzyme; before starting the IDH2 reaction with the addition of 10 µl of substrate mix containing 4 µM NADPH and 1.6 mM α-KG in the buffer described above. After a further 16 hours of incubation at room temperature, the reaction is halted, and the remaining NADPH measured through conversion of resazurin to resorufin by the addition of 25 µl Stop Mix (36 µg/ml diaphorase enzyme and 60 µM resazurin; in buffer). After one minute of incubation the plate is read on a plate reader at Ex544/Em590.

For determination of the inhibitory potency of compounds against IDH2 R140Q in an assay format similar to the above, a similar procedure is performed, except that the final testing concentration is 0.25 µg/ml IDH2 R140Q protein, 4 µM NADPH and 1.6 mM α-KG.

For determination of the inhibitory potency of compounds against IDH2 R140Q in a high throughput screening format, a similar procedure is performed, except that 0.25 µg/ml IDH2 R140Q protein is utilized in the preincubation step, and the reaction is started with the addition of 4 µM NADPH and 8 µM α-KG.

In Vitro Assays for IDH2m R140Q Inhibitors

The following describes the experimental procedures used to obtain the data in column 6 of Table 5.

Compounds are assayed for IDH2 R140Q inhibitory activity through a cofactor depletion assay. Compounds are preincubated with enzyme and cofactor, then the reaction is started by the addition of α-KG, and allowed to proceed for 60 minutes under conditions previously demonstrated to be linear. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 µl of 50× compound dilution series is placed, followed by the addition of 40 µl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 0.39 µg/ml IDH2 R140Q protein, 5 uM NADPH and 750 uM NADP. The test compound is then incubated for 16 hrs at room temperature with the enzyme and cofactors before starting the IDH2 reaction with the addition of 10 µl of substrate mix containing 8 mM α-KG (final concentration 1.6 mM) in the buffer described above. After a further 1 hour of incubation at room temperature, the reaction is halted, and the remaining NADPH measured through conversion of resazurin to resorufin by the addition of 25 µl Stop Mix (36 µg/ml diaphorase enzyme and 60 µM resazurin; in buffer). After one minute of incubation the plate is read on a plate reader at Ex544/Em590.

The data for various compounds of one aspect of the disclosure in the R132H enzymatic assay, R132C enzymatic assay, R140Q enzymatic assay, R132C cell-based assay, and R140Q cell-based assay as described above or similar thereto are presented below in Tables 4 and 5.

TABLE 4

Inhibitory Activities of Exemplary Compounds 1 to 6 against mIDH1

| Compound | IDH1 WT IC50 1 h | IDH1 WT IC50 16 h | IDH1 R132H IC50 1 h | IDH1 R132H IC50 16 h | WT/R132H IC50 1 h | WT/R132H IC50 16 h |
|---|---|---|---|---|---|---|
| 1 | 1.587 | 0.042 | 0.036 | 100 | 0.014 | 0.002 |
| 2 | 4.875 | 0.161 | 0.451 | 100 | 0.081 | 0.069 |
| 3 | 5.546 | 1.256 | 0.576 | 0.711 | 0.717 | 0.246 |
| 5 | 100 | 100 | 100 | 100 | 100 | 100 |
| 4 | 1.525 | 0.832 | 0.501 | 0.222 | 0.415 | 0.591 |
| 7 | 1.578 | 0.075 | 0.168 | 0.394 | 0.022 | 0.034 |

TABLE 5

Inhibitory Activities of Compounds 1 to 6 against mIDH2

| Compound | IDH2 WT IC50 1 h | IDH2 WT IC50 16 h | IDH2 R140Q IC50 1 h | IDH2 R140Q IC50 16 h | WT/R140Q IC50 1 h | WT/R140Q IC50 16 h |
|---|---|---|---|---|---|---|
| 1 | 0.41 | 0.037 | 0.193 | 0.021 | 0.488 | 0.04 |
| 2 | 1.2 | 0.209 | 0.552 | 0.146 | 1.709 | 0.264 |
| 3 | 100 | 5.063 | 2.34 | 1.555 | 100 | 7.715 |
| 5 | 100 | 100 | 100 | 100 | 100 | 100 |
| 4 | 100 | 100 | 1.301 | 3.51 | 100 | 100 |
| 7 | 0.910 | 0.098 | 0.430 | 0.059 | 1.232 | 0.125 |

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of treating a cancer comprising administering to a patient in need thereof a therapeutically effective amount of a purified compound or a pharmaceutically acceptable salt thereof, wherein the cancer is characterized by the presence of at least one mutation chosen from an IDH1 mutation or an IDH2 mutation and wherein the purified compound is selected from:

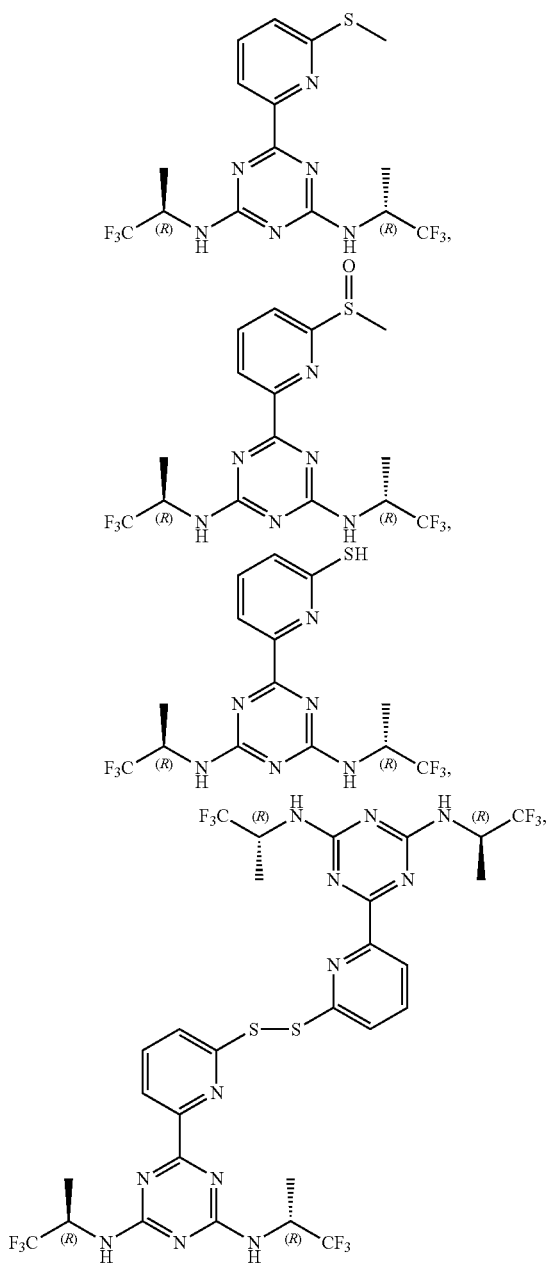

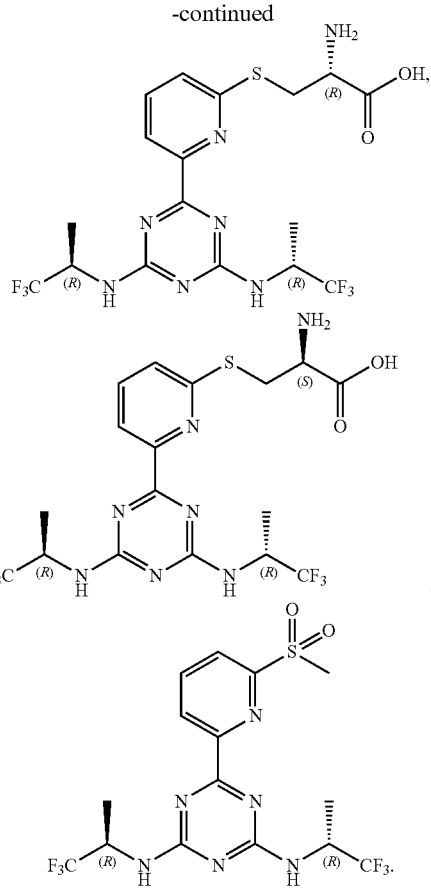

2. The method of claim 1 wherein the cancer is selected from glioma (including low grade glioma), glioblastoma (including secondary glioblastoma), grade II or III astrocytoma, grade II or III oligodendroglioma, acute myelogenous leukemia (AML), sarcoma, melanoma, non-small cell lung cancer (NSCLC), cholangiocarcinomas, chondrosarcoma, myelodysplastic syndromes (MDS), myeloproliferative neoplasm (MPN), colon cancer, and angio-immunoblastic non-Hodgkin's lymphoma (NHL) in a patient.

3. The method of claim 2, wherein the cancer is glioma.

4. The method of claim 3, wherein the glioma is a low grade glioma or a high grade glioma.

5. The method of claim 1, wherein the mutation is an IDH1 mutation.

6. The method of claim 5, wherein the IDH1 mutation is an R132X mutation.

7. The method of claim 6, wherein the IDH1 mutation is an R132H or R132C mutation.

8. The method of claim 1, wherein the mutation is an IDH2 mutation.

9. The method of claim 8, wherein the mutation is a R140X or R172X mutation.

10. The method of claim 9, wherein the mutation is a R140Q, R140W, or an R140L mutation.

11. The method of claim 9, wherein the mutation is an R172K or R172G mutation.

12. The method of claim 1, wherein the amount of the purified compound or pharmaceutically acceptable salt thereof administered to the patient is between about 1 and 5000 mg/day.

13. The method of claim 12, wherein the amount of the purified compound or pharmaceutically acceptable salt thereof administered to the patient is between about 1 and 1000 mg/day.

14. The method of claim 12, wherein the amount of the purified compound or pharmaceutically acceptable salt thereof administered to the patient is between about 1 and 500 mg/day.

15. The method of claim 1 wherein the purified compound is administered orally.

16. The method of claim 1 wherein the purified compound or composition is administered in combination with an additional therapeutic modality.

17. The method of claim 16 wherein the additional therapeutic modality is selected from radiation, surgical resection, anti-cancer medications, anti-epileptic medications, anti-seizure medications and anti-emesis medications.

18. The method of claim 17, wherein the anti-cancer medications are selected from chemotherapy with cytotoxic or cytostatic agents, targeted medications, antibody therapy, immunotherapy and hormonal therapy.

19. A method of treating a cancer comprising administering to a patient in need thereof a therapeutically effective amount of a composition comprising a purified compound or a pharmaceutically acceptable salt thereof, wherein the cancer is characterized by the presence of at least one mutation chosen from an IDH1 mutation or an IDH2 mutation and wherein the purified compound is selected from:

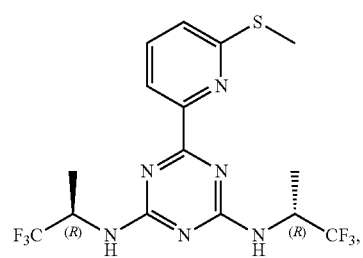

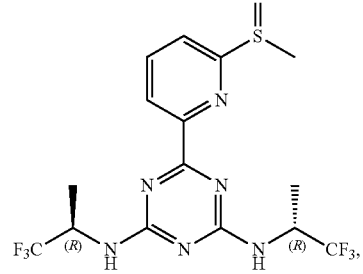

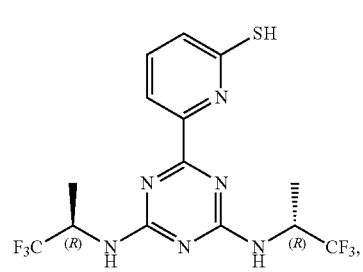

-continued

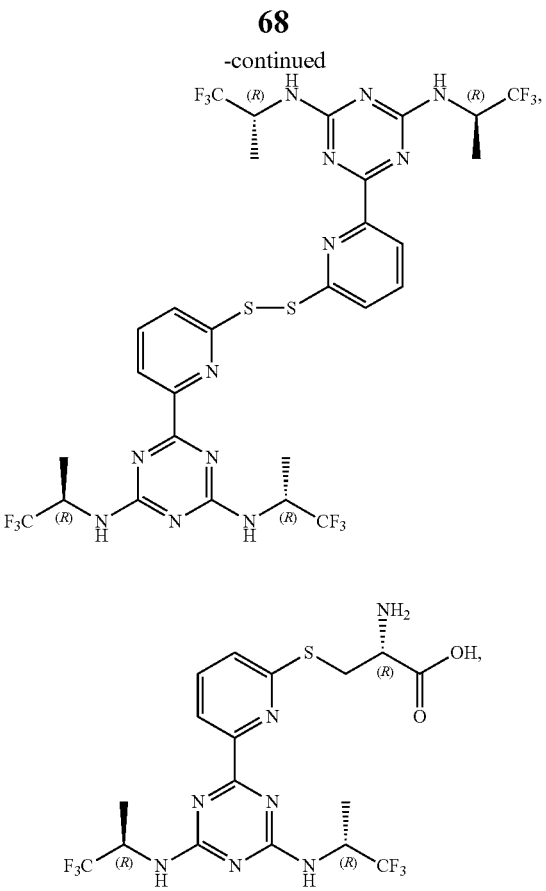

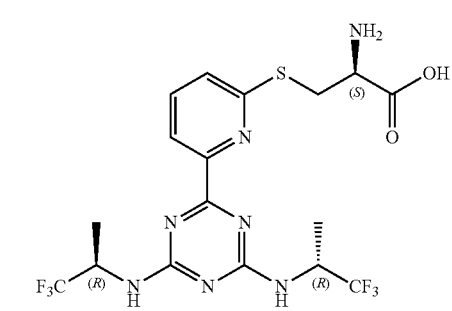

and

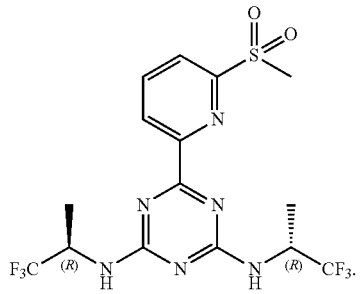

20. A method of treating a glioma in a subject in need thereof comprising administering to the subject a therapeutically effective amount of a purified compound or a pharmaceutically acceptable salt thereof, wherein the glioma is characterized by the presence of at least one mutation chosen from an IDH1 mutation or an IDH2 mutation and wherein the purified compound is selected from:

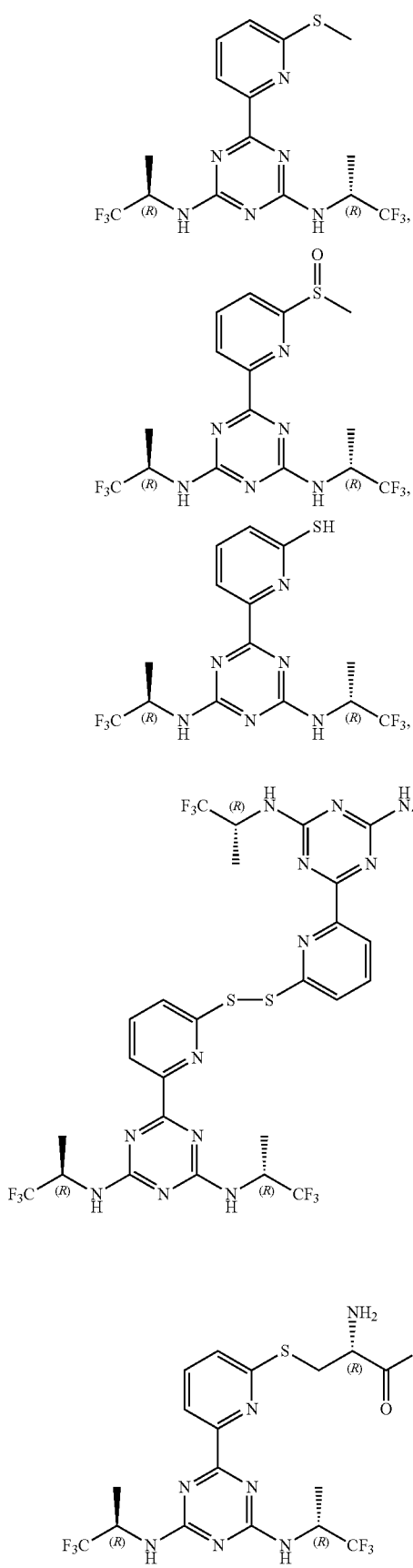

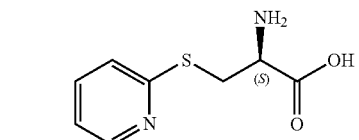

and

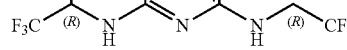

21. A method of treating a glioma comprising administering to a patient in need thereof a therapeutically effective amount of a composition comprising a purified compound or a pharmaceutically acceptable salt thereof, wherein the glioma is characterized by the presence of at least one mutation chosen from an IDH1 mutation or an IDH2 mutation and wherein the purified compound is selected from:

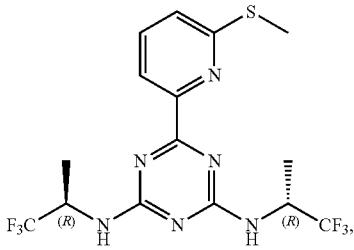

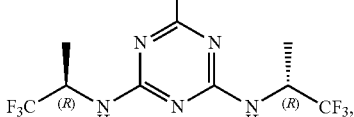

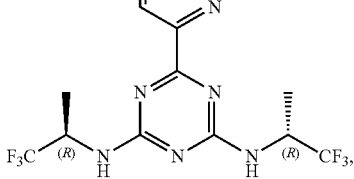

71
-continued
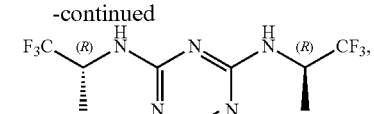
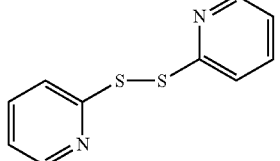
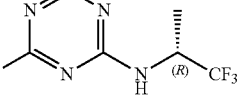
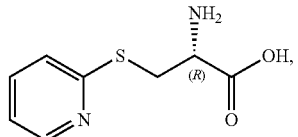
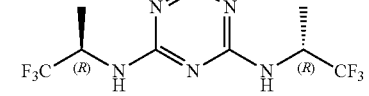
72
-continued
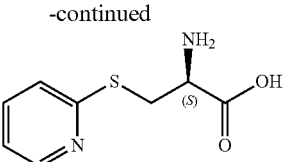
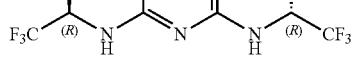
and
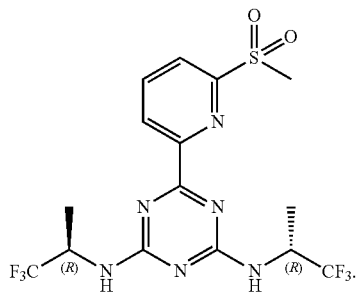
* * * * *